(12) United States Patent
Kil

(10) Patent No.: US 8,714,983 B2
(45) Date of Patent: May 6, 2014

(54) MULTI-PLAYER ROLE-PLAYING LIFESTYLE-REWARDED HEALTH GAME

(75) Inventor: David H. Kil, Santa Clara, CA (US)

(73) Assignee: Accenture Global Services Limited, Dublin (IE)

( * ) Notice: Subject to any disclaimer, the term of this patent is extended or adjusted under 35 U.S.C. 154(b) by 1727 days.

(21) Appl. No.: 11/751,856

(22) Filed: May 22, 2007

(65) Prior Publication Data

US 2008/0146334 A1 Jun. 19, 2008

Related U.S. Application Data

(63) Continuation-in-part of application No. 11/612,763, filed on Dec. 19, 2006, now Pat. No. 8,200,506.

(51) Int. Cl.
*A63B 69/00* (2006.01)
*G06Q 30/00* (2012.01)
*G09B 19/00* (2006.01)

(52) U.S. Cl.
USPC .......................... 434/247; 434/236; 705/14.12

(58) Field of Classification Search
USPC .......... 434/236, 350, 247, 323, 362; 705/2, 3, 705/14.1, 14.12; 481/1, 8; 482/8, 1
See application file for complete search history.

(56) References Cited

U.S. PATENT DOCUMENTS

| | | | | |
|---|---|---|---|---|
| 5,001,632 A * | 3/1991 | Hall-Tipping | ..................... | 463/7 |
| 5,813,863 A * | 9/1998 | Sloane et al. | .................. | 434/236 |
| 5,879,163 A * | 3/1999 | Brown et al. | .................. | 434/236 |
| 5,918,603 A * | 7/1999 | Brown | .......................... | 128/897 |
| 6,039,688 A | 3/2000 | Douglas et al. | | |
| 6,120,300 A * | 9/2000 | Ho et al. | ........................ | 434/332 |
| 6,302,789 B2 * | 10/2001 | Harada et al. | ..................... | 463/7 |
| 6,561,811 B2 * | 5/2003 | Rapoza et al. | ................. | 434/236 |
| 6,769,915 B2 * | 8/2004 | Murgia et al. | .................. | 434/236 |
| 6,817,979 B2 | 11/2004 | Nihtila | | |
| 7,091,976 B1 | 8/2006 | Ostermann et al. | | |
| 7,128,577 B2 | 10/2006 | Renaud | | |
| 7,379,066 B1 | 5/2008 | Ostermann et al. | | |
| 7,609,270 B2 | 10/2009 | Ostermann et al. | | |
| 7,671,861 B1 | 3/2010 | Ostermann et al. | | |
| 7,792,379 B2 | 9/2010 | Andres Del Valle | | |

(Continued)

OTHER PUBLICATIONS

Roizen, Michael F., Real Age Are You as Young as You can Be?, 1999, entire book, Cliff Street Books, New York, USA.

(Continued)

*Primary Examiner* — Peter Egloff
(74) *Attorney, Agent, or Firm* — Fish & Richardson P.C.

(57) ABSTRACT

Embodiments of the invention provide apparatuses, computer media, and methods for supporting lifestyle-reward health games, in which execution is altered based on health behavior of the participant. Input data indicative of the health behavior is obtained and converted into a gaming parameter. The gaming parameter is applied to the lifestyle-reward health game in order to alter the execution of the lifestyle-reward health game. A reward parameter for the participant may be determined based on a utility function, and the reward parameter is invoked when the participant is playing the life-reward health game. Feedback to the participant may be incorporated during the execution of the lifestyle-reward health game, where the feedback is indicative of the participant's health behavior. An avatar may be depicted during execution of the lifestyle-reward health game to illustrate a predicted health condition, in which the depiction is altered by changing the timeframe of the predicted health condition.

23 Claims, 11 Drawing Sheets

(56) References Cited

U.S. PATENT DOCUMENTS

| | | | |
|---|---|---|---|
| 7,953,294 | B2 | 5/2011 | Andres Del Valle |
| 8,014,589 | B2 | 9/2011 | Andres Del Valle |
| 8,033,996 | B2 | 10/2011 | Behar |
| 2002/0160883 | A1* | 10/2002 | Dugan ............................ 482/8 |
| 2003/0206170 | A1 | 11/2003 | Bickmore et al. |
| 2004/0002634 | A1 | 1/2004 | Nihtila |
| 2005/0021750 | A1 | 1/2005 | Abrams |
| 2005/0101845 | A1 | 5/2005 | Nihtila |
| 2005/0137015 | A1 | 6/2005 | Rogers et al. |
| 2005/0206610 | A1 | 9/2005 | Cordelli |
| 2005/0216529 | A1 | 9/2005 | Ashtekar et al. |
| 2005/0235062 | A1 | 10/2005 | Lunt et al. |
| 2006/0089543 | A1 | 4/2006 | Kim et al. |
| 2006/0105825 | A1* | 5/2006 | Findlay ............................ 463/4 |
| 2006/0143569 | A1 | 6/2006 | Kinsella et al. |
| 2006/0210045 | A1 | 9/2006 | Valliath et al. |
| 2006/0256132 | A1 | 11/2006 | Shin et al. |
| 2007/0050715 | A1 | 3/2007 | Behar |
| 2008/0174795 | A1 | 7/2008 | Andres Del Valle |
| 2008/0175517 | A1 | 7/2008 | Andres del Valle |
| 2008/0187246 | A1 | 8/2008 | Andres Del Valle |
| 2008/0201442 | A1 | 8/2008 | Ostermann et al. |
| 2009/0325701 | A1 | 12/2009 | Andres Del Valle |
| 2010/0042697 | A1 | 2/2010 | Ostermann et al. |
| 2011/0064331 | A1 | 3/2011 | Andres Del Valle |
| 2011/0157175 | A1 | 6/2011 | Andres Del Valle |

OTHER PUBLICATIONS

Schlessinger, Leonard, et al. "Archimedes: a new model for simulating health care systems—the mathematical formulation," Journal of Biomedical Informatics, 2002, pp. 37-50, Elsevier Science, USA.

Giles, Jim. "Concept of 'personal space' survives in virtual reality," 2006, pp. 1-3, Linden Research, Inc. USA.

Yee, Nicholas "The Psychology of MMORPGs: Emotional Investment, Motivations, Relationship Formation, and Problematic Usage," Avatars at Work and Play: Collaboration and Interaction in Shared Virtual Environments, 2006, pp. 1-31, Springer-Verlag, London, UK.

Ahn, Hyungil, et al. "Affective Cognitive Learning and Decision Making: The Role of Emotions," 2006, pp. 1-6, Austria.

Kent, S.L. "Making an MMOG for the Masses," GameSpy, Oct. 10, 2003, pp. 1-11, USA.

Nussbaum, B. "Is Wii the New iPod—and More Important than iPhone?" BusinessWeek, Jan. 9, 2007, pp. 1-12, USA.

Schiesel, S. "Online Game, Made in U.S., Seizes the Globe," The New York Times, Sep. 5, 2006, pp. 1-5, USA.

Wingfield, N. "Nintendo's Wii Outsold Other Consoles in February" The Wall Street Journal, Mar. 19, 2007, pp. B3, USA.

* cited by examiner

MULTI-PLAYER ROLE-PLAYING LIFESTYLE-REWARDED HEALTH GAME

This application is a continuation-in-part of co-pending U.S. patent application Ser. No. 11/612,763 entitled "Integrated Health Management Platform" and filed on Dec. 19, 2006, the entire disclosure of which is hereby incorporated by reference.

FIELD OF THE INVENTION

This invention relates generally to healthcare management. More particularly, the invention provides apparatuses, computer media, and methods for supporting lifestyle-reward health games, in which execution is altered based on health behavior of the participant.

BACKGROUND OF THE INVENTION

The U.S. healthcare industry is a $2T economy with the rate of growth far exceeding that of general inflation. With the aging global population, the current healthcare crisis is expected to worsen, threatening the health of the global economy. The existing healthcare ecosystem is zero-sum. The recent pay-for-performance (P4P) experiment by the National Health Services in the United Kingdom resulted in mixed outcomes with incentive-based payments far exceeding the budget with uncertain improvements in patient health. On the other hand, a recent study on the sophistication of healthcare consumers reveals that there is little correlation between consumers' perception of care and the actual quality of healthcare delivered as measured by RAND's 236 quality indicators. Furthermore, given the high churn rate and the propensity of employers to seek the lowest-cost health plan, payers are motivated to focus primarily on reducing short-term cost and carving out the cream-of-the-crop population, resulting in perverse benefit design.

In order to control the cost of healthcare, it is important to engage the insured individuals themselves. In general, as an individual becomes more cognizant about a healthy life style, the more likely the individual will live a life style that is more conducive to the individual's health.

Healthcare and fun typically do not go together. A prior art health-simulation model estimates one's probability of developing a chronic disease in the future based on multiple parameters encompassing clinical data, disease markers, and lifestyle. While adequate for scientific research, it is not a fun way to engage consumers by threatening them with statistical jargons, such as "Your risk for diabetes is 5.2 times higher because your BMI puts you in the highest 5 percentile."

A prior art Web-based health-risk assessment (HRA) asks a large number of questions to calculate one's real age, which may be different from the actual chronological age depending on her health habits and existing disease conditions. The idea is that the more healthy habits one has, the younger one is in comparison to one's actual earth age. Unfortunately, consumers bemoan the fact that the guidelines are written for the masses and that what may be OK for the masses is not good for certain individuals. One participant commented: "I found many interesting things in this book that is written for the masses. However, like exercising, everyone needs to decide or get a professionals opinion about what is good for them as an individual. I had followed the recommendations of the book for the last 9 months to a tee besides going to the website to get my "Realage" down. I just experienced a kidney stone that needed to be removed. For anyone that has been through a stone ordeal knows that it is equal in pain to childbirth or more so according to my urologist. A leading contributor of my stone was the increased intake of calcium, vitamin D, and Vitamin C that I took based on the recommendations of this book. Were there other factors? Probably. However, what is good for one person may not be good for all. So proceed with caution. Again, the book did enlighten me in many areas."

A prior art Web-based questionnaire that calculates one's risk of developing several chronic diseases in the future based on participant-provided information on previous diagnoses, lifestyle, behavior, family disease history, and physiological data. Unfortunately, these programs are geared towards collecting information from consumers, not engaging them in an interactive game that promotes health in a fun way.

A prior art fitness and wellness offering includes a shoe sensor, which is essentially a wireless pedometer that works seamlessly with iPod Nano™. While the consumer is running, the shoe sensor transmits data to a wireless receiver attached to the iPod Nano, which then calculates time elapsed, distance traveled, and speed, which can be recited to the consumer regularly or on demand. When the participant (user) connects the iPod™ to iTunes$^{SM}$ for synchronization, the stored data in the iPod is automatically uploaded to a Web portal, where the consumer can check his progress against his goals and compare his performance with those of the global pool of runners. Every time the consumer sets a new record in speed or endurance, a celebrity's recorded voice (for example, Lance Armstrong) congratulates him as an extra dose of positive reinforcement. The Web portal also has a community site, where people can sign up other members for fitness challenge. While this approach is a very good start, supported activities are limited to running, and the level of consumer understanding and solution tailoring is rather weak.

Another prior art offering includes a wearable sensor (armband) that measures arm movements through a 2-axis accelerometer, skin temperature, heat flux, and galvanic skin response to compute caloric expenditure over time. Using annotated life-activity data matched to pre-recorded caloric expenditure data, a life-activity recognition algorithm differentiates low-energy states (couch potato) from high-energy activities. The participant has an option of journaling food entry so that she can keep track of daily caloric surplus or deficit.

A prior art wellness program rewards healthy behaviors with health miles (similar to frequent-flyer miles) that can be redeemed for merchandise from participating merchants, e.g., a pedometer, or a gym-membership discount. Examples of healthy behaviors encompass checking biometric signals at a kiosk located at various health clubs, pedometer readings, and filling out online health questionnaire.

Another prior art offering uses a GPS-enabled cellphone to monitor one's fitness activities, consisting of primarily running. An application in cellphone records location over time to compute distance, duration, speed, and calories expended using height and weight information entered by the participant during registration. The participant can create and share blogging with other running enthusiasts. They can also publish their favorite workout routes, hoping to meet new friends.

The above prior art offerings have the following common attributes:
- Sensor and/or self-reported data
- Limited analytics and data visualization
- Limited interaction with other participants
- Geared to hard-core health enthusiasts
- Not much entertainment value to the general public with different needs Social networking is another avenue that can draw together consumers who share common interests. A prior art social networking system works by having participants create their profiles and build their social networks by similarity matching and invitation to join via email. However, while useful for developing personal relationships through social networks, current social networking sites offer mostly entertainment services having little to do with improving one's health. A prior art alpha site caters to the health conscious by having them share their experiences in healthy eating, exercise alternatives, and fitness goals, such as running a marathon. Unfortunately, the site to have lost traction among health and wellness enthusiasts because of poor consumer experience. Furthermore, most of the information can be found easily through yellow pages and search engines.

Massively multi-player role-playing online (MMPRPO) games often appeal to consumers by letting each consumer (1) create an avatar of his fantasy, (2) have fun in exploring new environments and conquering new challenges through judicious social networking and opportunistic thinking, and (3) advance the skill levels and social status each time he completes tasks (defeating or slaying monsters) as a form of continuous positive reinforcement. Many of these games may be so addictive that some spend many hours playing the game to improve the status and trade highest-class avatars to the highest bidders on eBay. Although fun, the addictive nature coupled with the sedentary playing style may even wreak havoc with one's health. Furthermore, many regard playing the game as a second job and thus no longer a fun activity.

Besides MMPRPO, a prior art game encourages physical actions during gaming. The game uses a remote controller with accelerometers and infrared detectors to detect its position in the three-dimensional coordinate space. The controller communicates to the game console via Bluetooth and this configuration allows the participant to play the game using both physical movements and buttons on the remote controller, thus embedding physical activity into a gaming experience.

The above prior art examples illustrate the strong market need to incorporate fun and excitement into gaming that promotes health and wellness to participants.

BRIEF SUMMARY OF THE INVENTION

Embodiments of the invention provide apparatuses, computer media, and methods for supporting lifestyle-reward health games, in which execution is altered based on health behavior of the participant. Input data indicative of the health behavior is obtained and converted into a gaming parameter. The gaming parameter may be applied to the lifestyle-reward health game in order to alter the execution of the lifestyle-reward health game.

With one aspect of the invention, obtaining input data indicative of health behavior of a participant is obtained and converted into a gaming parameter. The gaming parameter is applied to a lifestyle-reward health game in order to alter execution of the lifestyle-reward health game to be indicative of the health behavior of the participant.

With another aspect of the invention, a health condition of a participant is predicted from input data and a gaming parameter is determined. The causality of the health condition may be assessed based on one or more health factors.

With another aspect of the invention, a reward parameter for a participant is determined based on a utility function and the reward parameter may be invoked when the participant is playing the life-reward health game. The utility function may be estimated from a projected performance difference exhibited by the participant before and after a reward, if provided.

With another aspect of the invention, feedback to a participant is incorporated during the execution of the lifestyle-reward health game, where the feedback is indicative of the participant's health behavior. The feedback may be tailored to or otherwise based on a preference of the participant, in which the preference is determined from data comprising immersive user data.

With another aspect of the invention, a trait of a participant is inferred from input data. The trait is translated into a gaming parameter so that a health consequence of the trait can be provided to the participant while executing a lifestyle-reward health game.

With another aspect of the invention, metadata is determined from a participant's activities or social encounters. An execution of a lifestyle-reward health game is altered based on the metadata.

With another aspect of the invention, a depiction is provided on an avatar during execution of a lifestyle-reward health game to illustrate a predicted health condition. The depiction on the avatar may be altered, for example, by changing the timeframe of the predicted health condition.

BRIEF DESCRIPTION OF THE DRAWINGS

The present invention is illustrated by way of example and not limited in the accompanying figures in which like reference numerals indicate similar elements and in which.

DETAILED DESCRIPTION OF THE INVENTION

Figure 1:
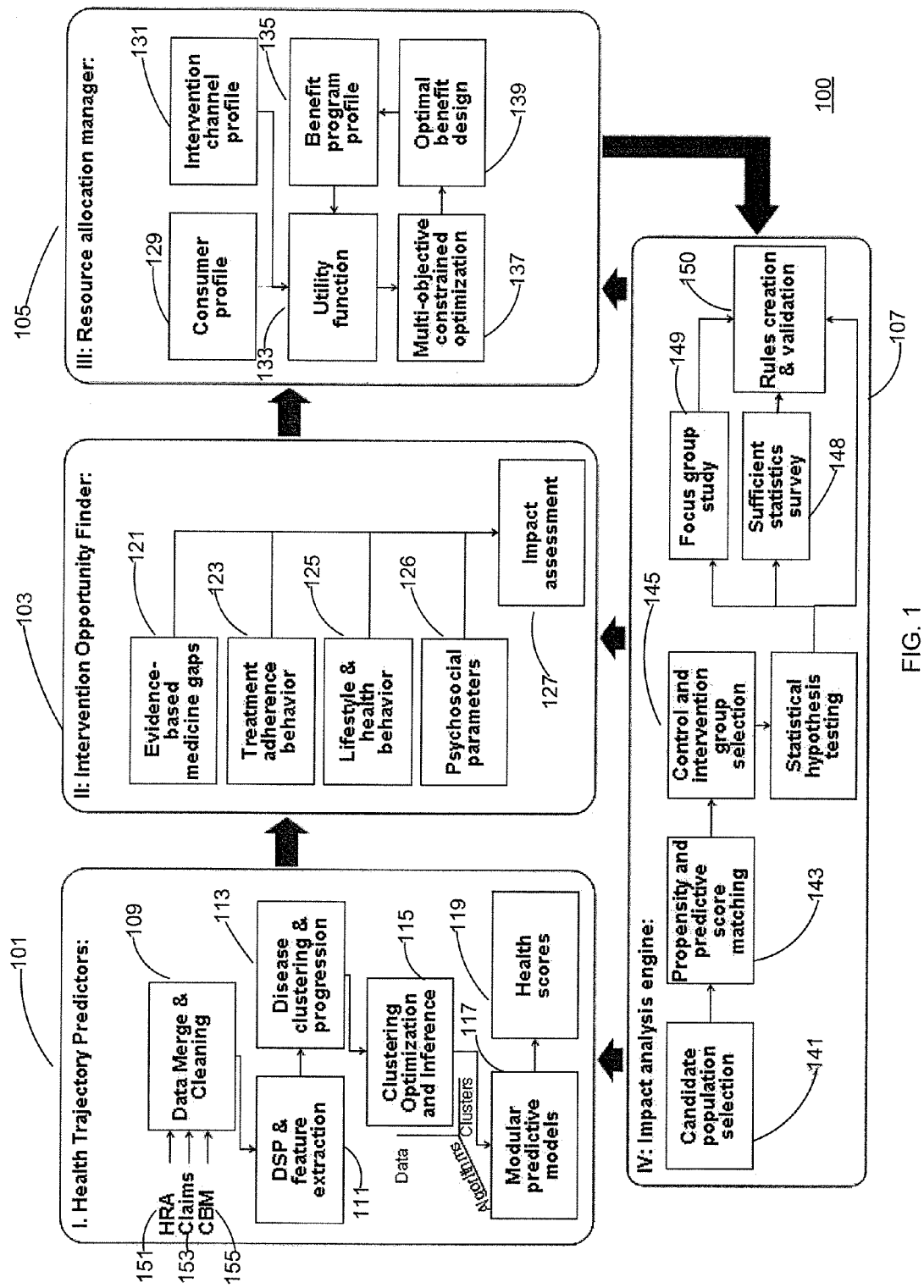
FIG. 1 shows an architecture of an integrated health management (IHM) platform in accordance with an embodiment of the invention.

Integrated Health Management Platform in a Service Oriented Architecture (SOA) Framework FIG. 1 shows an architecture of integrated health management (IHM) platform 100 in accordance with an embodiment of the invention. IHM platform 100 creates for payers a virtuous circle of integrated informatics leading to improved and real-time decision making leading to healthier members leading to improved profitability and cost savings leading to improved market share. For consumers who must share an increasing burden of medical costs, the execution of IHM platform may lead to improved health and subsequent cost savings. In the following discussion, a consumer may be an employee of a company or an individual choosing a healthcare plan from a plurality of plans and consuming products/services from various healthcare stakeholders. An objective of the consumer is to maximize benefits associated with good health by choosing a healthcare plan that is "best" for the individual or his/her family and improving health through timely preventive and proactive health actions.

The IHM platform consists of the following four components:

1. Multimode health-trajectory predictors module 101: Instead of focusing on predicting future cost alone using claims data as most predictive models do now, multimode health-trajectory predictors leverage claims data 153, self-reported data 151, and consumer behavior marketing data 155, coupled with inference engines 115, to provide a comprehensive set of future attributes useful to assess the level of impact through various consumer-engagement channels. Claims data 153 may include medical claims, pharmacy claims, prior authorization, and lab results (e.g., blood tests) for a consumer. Consumer-engagement channels may encompass secure e-mails, Interactive Voice Recording (IVR) calls, cellphone text messages, and nurse calls. Data Merge & Cleaning 109 performs extract-transform-load (ETL) of disparate data assets to form a consumer-centric view while cleaning data prior to weak-signal transformation through digital signal processing (DSP) and feature extraction 111. Disease clustering and progression module 113 subsequently forms disease clusters and estimates disease progression probabilities. Clustering optimization & inference 115 performs clustering using attributes that are meaningful from the perspective of predicting future health trajectories and impactability with the inference engine filling in unobserved variables using the instantiated variables. A modular predictive model is developed for each consumer cluster so that a collection of locally optimized predictive models can provide a globally optimal performance 117. Finally, a set of health scores encompassing health scores, behavior/lifestyle scores, engagement scores, impact scores, data-conflict scores, cost scores, and clinical scores is output 119.

2. Targets-of-opportunity finder 103: Leveraging consumer-understanding technologies, an evidence-based-medicine (EBM) supercharger (shown as EBM supercharger 300 in FIG. 3), and an autonomous insight crawler, one can identify targets of opportunities in various consumer touch points. The four major opportunities lie in clinical gaps 121, treatment adherence 123, lifestyle/behavior 125, and psychosocial parameters 126. Impact assessment is made based on the aggregate future impact of all the identified targets of opportunities 127.

3. Resource-allocation manager 105: Resource-allocation manager (RAM) 105 funnels the right members to the right consumer touch points at the right time by maximizing multi-objective functions. Also included in RAM 105 are consumer-understanding technologies and iterative benefit design borrowing salient concepts from adaptive conjoint analysis, predictive modeling, and Pareto multi-objective optimization. Furthermore, mixing-in currently available technologies into consumer touch points in conjunction with dynamic progressive content tailoring allows one to go beyond the typical nurse-based care model, which is inherently not scalable especially with the projected worsening nurse shortage in the labor market. (Resource-allocation manager 105 is Pareto efficient if no consumer can be made better off without another consumer being made worse off.) The fundamental idea here is building a multi-objective constrained optimization engine 137 as a function of consumer, intervention-channel, benefit-program profiles (129, 131, 135) and utility functions 133 derived from the impact analysis engine.

4. Impact-analysis engine 107: This module tells one what works for which population segments, by how much, and why in a drilldown mode. It facilitates the use of utility functions in the framework of resource-allocation optimization as done in defense battlefield resource management. The methodology employed uses predictive modeling, combinatorial and stochastic feature optimization with respect to outcomes, and propensity-score shaping. After selecting candidate population for analysis 141, one performs thorough matching in the two-dimensional space of propensity and predictive scores 143 to create control and intervention groups 145 for an "apple-to-apple comparison." One then create rules of engagement for statistically significant outcomes, which are further validated through focus-group study 149 and survey using the minimum number of necessary questions 148. Validated rules 150 are stored in the master rules database for production implementation.

The four above components 101-107 complement one another and are ideally suited to assessing the incremental benefits of bringing new data assets and business processes into enterprise operations. In order to facilitate integration into and compatibility with typical payer enterprise applications, the IHM implementation (e.g., IMH platform 100) adheres to an enhanced Service Oriented Architecture (SOA) framework. A key idea here is maximizing synergy among business process primitives, data models, and algorithm models so that one can reduce latency between the generation of actionable knowledge and its production implementation.

Figure 1A:
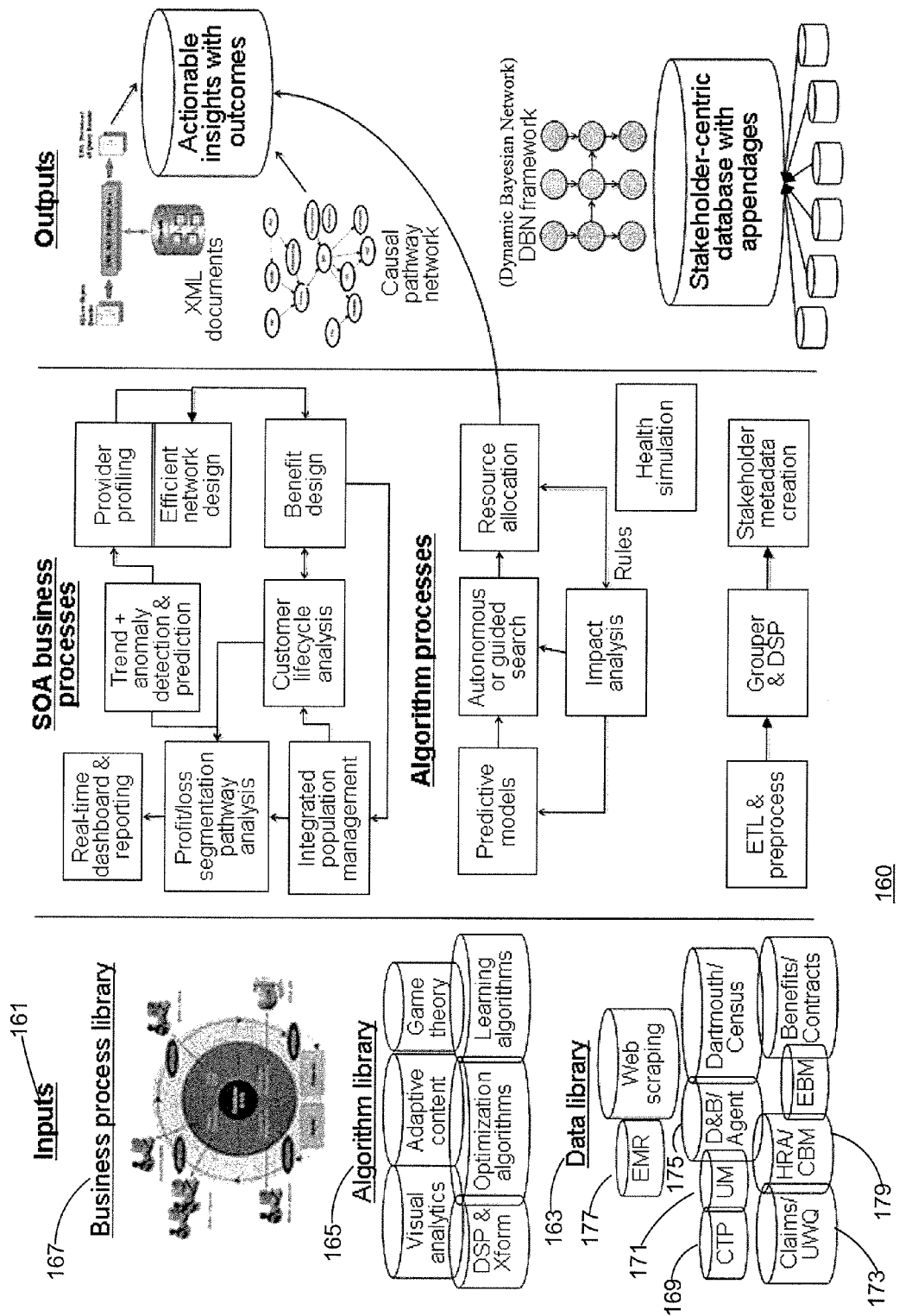
FIG. 1A shows a Service Oriented Architecture (SOA) framework in accordance with an embodiment of the invention.

FIG. 1A shows Service Oriented Architecture (SOA) framework 160 of IHM platform 100 in accordance with an embodiment of the invention. Framework 160 increases synergy in data models, mathematical models, and business-process models that are important in ensuring the success of IHM Platform 100. Inputs 161 consist of data library 163, algorithm library 165, and business-process libraries 167, which get updated with the latest discoveries. The processing layer uses the building blocks of business processes and algorithms tailored to underlying data models to produce intermediate processing outputs as well as actionable insights that feed to multimedia outputs for dissemination to the key stakeholders.

Data library 163 includes Consumer Touch Points (CTP) 169, Utilization Management (UM) 171, Underwriting Questionnaire (UWQ) 173, D&B: Dun & Bradstreet (D&B) database 175, Electronic Medical Records (EMR) 177, and Health Risk Assessment (HRA) database 179.

Multimode Health-Trajectory Predictors

Figure 2:
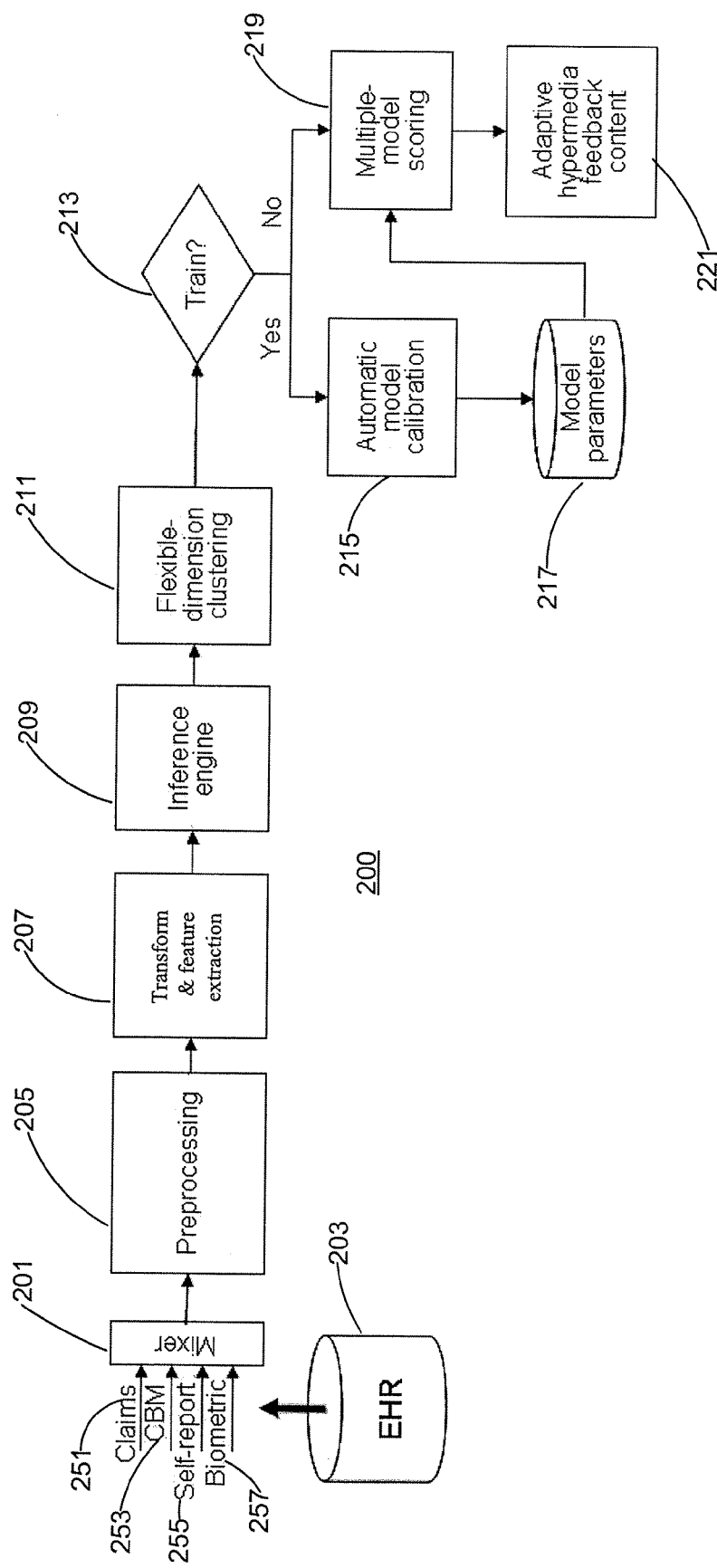
FIG. 2 is a flow chart showing a method of determining multimode health-trajectory predictors in accordance with an embodiment of the invention.

FIG. 2 shows process 200 for determining multimode health-trajectory predictors in accordance with an embodiment of the invention. Instead of focusing on cost prediction, multimode health-trajectory predictors attempt to understand current and predict transitions in Bayesian relationships among the many semi-orthogonal outcomes attributes so that one can maximize positive impact through delivering the right intervention touch points to the right consumers at the right time before adverse transitions occur.

In healthcare, predictive models are used to improve underwriting accuracies and to identify at-risk members for clinical programs, such as various condition-centric disease management programs. Typically, prior art predictive modes predict year-2 cost using year-1 payer claims data. Some prior art predictive modeling vendors predict future inpatient or emergency-room episodes since they represent high-cost events. The emphasis on cost makes sense given that the impetus for predictive models came from private and government payers struggling with rising healthcare costs.

Focusing on cost alone ignores the complex, multifaceted nature of healthcare consumers. Knowing future cost with R-sq of 10-25% is different from being able to impact the future health trajectory of each consumer. For example, it may be more beneficial to touch John suffering from pre-diabetic conditions with body mass index (BMI) of 32 than to intervene on behalf of Mark who has to go through kidney dialysis three times a week because of end-stage renal disease. From a cost perspective, Mark may be 20-40 times more expensive. But from an impact perspective, John would be a better candidate because his current conditions are more amenable to actions that can be taken now to prevent unpleasant consequences in the near future.

As a result of cost emphasis, prior art predictive models extract a standard set of features from Rx and/or medical claims data and apply linear regression or neural networks to predict year-2 cost. Typical features include disease flags and year-1 summary cost and utilization statistics, such as average inpatient cost per month, average Rx cost per month, # of physician visits per month, etc. Some predictive models divide the population into sub-groups using inputs from clinicians with the goal of designing a model tailored to each sub-group (MedAI). However, it may be quite difficult to design optimal clusters given the complexities of and interplays among the many factors that determine future health trajectories.

In order to address the shortcomings of the current generation of predictive models, an embodiment of the invention incorporates the following concepts:
1. Use of input data such as claims data 251, self-reported data 255, consumer behavior marketing (CBM) data 253, and biometric data 257 is augmented with inference engine 209 to predict multiple semi-orthogonal attributes with the goal of finding the best way to engage and motivate healthcare consumers to create positive impact. Input data is typically provided by electronic health record (EHR) database 203. Not everyone will have all the data assets. Therefore, key unknown variables need to be estimated using inference engine 209.
2. Flexible-dimension clustering process 211 creates an optimal set of consumer clusters from an impact perspective instead of using the same old disease hierarchy to create disease-centric consumer clusters.
3. Adaptive hypermedia content creation 221 leverages a comprehensive understanding of consumer needs and how to best provide a positive impact.

As shown in FIG. 2, inputs include:
Claims data 251: It is comprised of Rx/med/lab data, utilization-management (UM) data including pre-authorization, Rx/med benefit data, program touch-point data, Web log data, and limited member demographic data.
Consumer behavior marketing (CBM) data 253: This externally purchasable data provides inferred behavior, lifestyle, and attitudinal information on consumers from their demographic data and credit history.
Self-reported data 255: This includes health risk assessment (HRA), ecological momentary assessment (EMA), and experience sampling method (EMA) data administered through multiple communication channels, such as the Internet, cellphone, set top box, etc.
Biometric data 257: This encompasses data from wearable sensors (Bodymedia's BodyBugg™, Nike+ shoe sensor, polar band) and attachable sensors (glucometer, blood-pressure cuff, spirometer, etc.) transmitted through wired or wireless networks.

As shown in FIG. 2, processing includes:
Mixer 201: Not everyone will have all the data elements. Therefore, mixer 201 organizes incoming data into a schema appropriate for frame-based dynamical data processing. Furthermore, it differentiates between 0 and an empty set $\phi$.
Preprocessing 205: This step performs secondary data audit and consumer-centric data structure generation. Primary data audit occurs during data creation in enterprise data warehouse (EDW).
  1) Data audit: Outliers are normalized using multi-pass peak-shearing. Multiple debit/credit entries and ghost claims are eliminated. It looks for potential gender/age mismatch errors (grandmother or father giving birth to a baby or a premature baby's neonatal claims being assigned to his or her parents) using a look-up table.
  2) Consumer-centric data structure generation: For each consumer, we create an efficient data structure from memory and processing perspectives. It is a hierarchical structure encompassing the entire consumer touch-point suite of channels.
Transform 207: This step creates various bandpass-filtered maps over time. For instance, International Classification of Disease (ICD) 9/10 codes from medical claims and National Drug Codes (NDC) from Rx claims are converted into hierarchical condition-versus-time maps to facilitate the analysis of disease progression and the creation of disease clusters. Moreover, such a representation can help one to infer behavioral patterns from linking discrete events or following medication adherence for managing chronic conditions. A combination of ICD and Current Procedure Terminology (CPT) codes is used to derive Milliman & Robertson (M&R) categories over time, which is useful in assessing the utilization of various service types (inpatient, outpatient, emergency room, physician office visit, etc.) over time. Biometric data is processed through a large number of transformation algorithms, such as the fast Fourier transform, wavelet transform, local cosine transform, ensemble interval histogram, etc., in order to glean locally dynamic behaviors over time. Due to the infrequent nature of HRA and CBM data (i.e., people do not change their behavior or lifestyle every hour), locally dynamic behaviors serve as anchor points that vary much more slowly so that one can investigate the cumulative effects of linked local events over time on behavior change. The entire transformation process is analogous to multi-rate signal processing. At the end of transform, we extract a large number of static and dynamic features from each transformation space, as well as higher-order linked attributes spanning multiple transformation spaces in order to glean insights into disease clustering, disease progression, and their interplay with the consumer's psychosocial behavioral traits.

Inference engine 209: Knowing certain unobserved traits can be quite useful in devising tailored intervention strategies. Let $x_{claims}$, $x_{CBM}$, $x_{SR}$, and $x_{bio}$ represent the four data sets as previously discussed. If knowing one's body mass index (BMI) is desirable, one first builds modular predictive models from the sub-population that has BMI data such that $P(BMI|x_{claims})$, $P(BMI|x_{CBM})$, etc. constitute a feasible set of models for predicting BMI conditioned upon having other data assets. This model can be in the form of Bayesian networks, regression or classification algorithms leveraging parametric and non-parametric learning algorithms.

Flexible-dimension clustering 211: This is an iterative process leveraging multiple fitness functions and predictive models as part of clustering. This step generates a set of clusters for each outcomes variable such that the output dispersion compression is maximized for improved prediction accuracy.

1) For each outcomes variable, one performs feature optimization to find a sufficient-statistics feature subset.
2) One performs clustering using k-means, expectation-maximization (EM), and Kohonen's self-organizing feature map. After clustering, there are $N_C$ clusters for each outcomes variable. For each cluster, one calculates the dispersion $\sigma_i$, i=1, . . . , $N_C$ of each of the outcomes distributions and compare it with the overall dispersion $\sigma_T$ from the entire population. The dispersion-compression ratio (DCR) $r_i = \sigma_T/\sigma_i > \gamma$, where $\gamma > 1$, is a predetermined dispersion-compression threshold for accepting the $i^{th}$ cluster based on its ability to compress the outcomes distribution. One creates a set of samples that pass the DCR test.
3) For the samples that do not pass the first DCR test, repeat steps 1-2 until there is no sample left or the number of remaining samples is less than the minimum sample size.

Automatic model calibration 215: In real-world problems, data characteristics remain rarely stationary over time. With process 200, step 213 determines whether training is needed to update process 200 for new medical developments. For example, introduction of new medical technologies and drugs, changes in benefit plans and fee-reimbursement schedules, changing demographics, and even macroeconomic cycles can affect data characteristics. Built-into the automatic model calibration algorithm 215 is a data-mismatch estimator that keeps track of statistical parameterization of key data assets over overlapping time frames and consumer clusters after removing secular trends, e.g., medical-cost inflation. Model parameters are updated and stored in model parameters database 217. During model initialization and subsequent re-calibration, the following takes place:

1) Perform preprocessing step 205, transform step 207, inferring step 209, and flexible dimension clustering step 211
2) Feature optimization for each consumer cluster and outcomes variable using combinatorial and stochastic algorithms
3) Model performance tuning to find the point of diminishing returns
4) Multiple-model combining Multiple-model scoring 219: Once process 200 has been trained, multiple-model scoring 219 is performed for input data 251-257. One generates the following health scores:

1) Health scores as a function of current chronic conditions and predicted disease progression
2) Behavior and lifestyle scores computed heuristically as a function of reported, observed (medication adherence, frequent ER visits, the level of interaction with care-management nurses, etc.), and inferred behavior and lifestyle attributes
3) Engagement scores as a function of reported, observed, and inferred psychosocial and collaborative-filtering parameters
4) Impact scores working in concert with evidence-based-medicine (EBM) supercharger 300 and utility functions associated with targets of opportunities and derived from the impact-analysis engine
5) Conflict scores as a function of discrepancies between reported and observed behavioral/lifestyle factors and claims data
6) Cost scores for multiple future time periods in chronic vs. acute categories
7) Clinical utilization scores in terms of inpatient, emergency room/urgent care centers, medication, etc.

Adaptive hypermedia content generation 221: This module generates a tailored report of 1-2 pages succinctly summarizing current health conditions, likely future states, targets of opportunities, action plan, and benefits with drilldown menu.

Figure 3:
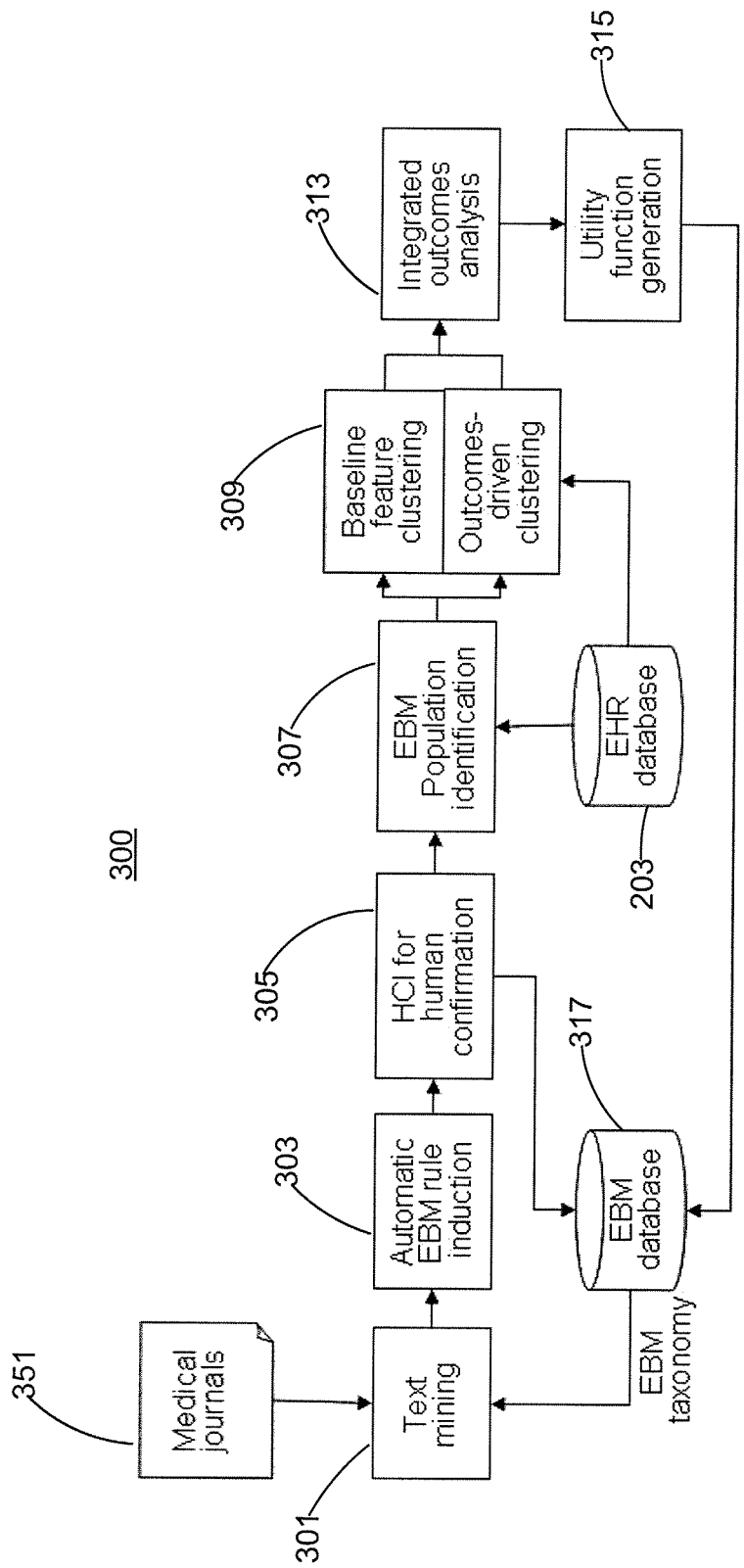
FIG. 3 shows a flow diagram for an evidence-based medicine supercharger in accordance with an embodiment of the invention.

In accordance with an embodiment of the invention, process 200 provides outputs including:

Consumer-centric metadata for a comprehensive view (both tabular and scientific visualization) of each consumer with appendages linking consumer-centric metadata to various stakeholders to facilitate stakeholder-centric data transformation Health scores Adaptive hypermedia content tailored to each consumer Evidence-Based Medicine Supercharger FIG. 3 shows a flow diagram for evidence-based medicine (EBM) supercharger 300 in accordance with an embodiment of the invention. From an EBM guideline or a medical journal article 351, evidence-based-medicine supercharger 300 generates a set of multidimensional inferred and observed utility functions, which is an essential ingredient in developing optimal resource allocation strategies. The utility function can be multidimensional at multiple levels of granularity in terms of patient or consumer clusters, leading to an M×N matrix, where M and N represent the number of utility components or objectives and the number of consumer clusters, respectively. For example, consumer clusters generated from the health-trajectory predictors may encompass the following groups: (1) those who are generally healthy from a claims perspective, but exhibit poor health habits in terms of high BMI and "couch-potato" characteristics; (2) those who suffer from chronic illnesses amenable from a lifestyle intervention, such as diabetes and cardiovascular disease; (3) people who have multiple co-morbid conditions, but one cannot find treatment-related claims records (N=3). From a segmented drilldown impact analyses of three intervention channels (Interactive Voice Response (IVR), health behavior coaching, and case management (M=3)), one determines that the most effective intervention channels for the three population clusters are (IVR, health behavior coaching), (health behavior coaching), (case management and health behavior coaching), respectively. The utility function is a 3×3 matrix, where each element $x_{ij}$ contains a utility score or return on investment for the $i^{th}$ intervention channel applied to the $j^{th}$ consumer cluster.

In accordance with an embodiment of the invention, evidence-based-medicine supercharger 300 includes:

Input databases:
1) EBM database 317: It consists of EBM rules, taxonomy for inducing rule parameters from medical journal, population parameters, rule strength, mapping look-up tables that map condition and drug names to ICD-9 and NDC, respectively, and utility function. Population parameters encompass inclusion and exclusion criteria. Rule strength is a function of publication rank using a page-ranking algorithm, author prestige based on the number of connections in the publication network, journal prestige based on the number of circulation, sample size, percentage of total cost affected, longitudinal duration, and the number of corroborating articles. The EBM taxonomy facilitates efficient induction of EBM-rule parameters from an exemplary journal abstract as shown in the Appendix. More algorithmic details will be discussed in the processing-algorithm subsection.
2) Electronic Health Records (EHR) 203: This database contains claims data 251, self-reported data 255, and consumer behavior marketing (CBM) data 253.

Processing algorithms

Text mining 301: The Appendix shows a semi-structured abstract from an article published in the New England Journal of Medicine. Instead of using a bag-of-words or natural-language-processing feature vector and a Naïve Bayes classifier to rank an abstract, one simply detects whether an abstract reports an outcomes study or not. This is a much easier problem and defers the strength-of-evidence classification until after integrated outcomes analysis. Next, one uses a combination of key words, tf*idf text weights (in which the importance of a word is based on its frequency of occurrence in a document and normalized by its natural frequency of occurrence in a corpus) with stemming and stop words, and distance measures from key words to fill in the hierarchical tree EBM database fields in the areas of:
1) Type of outcomes research
2) Patient characteristics: size, dropout rate (if available), characteristics in terms of inclusion and exclusion criteria, longitudinal duration, and trigger criteria
3) Reported results The distance measures are necessary to leverage lexical analysis to understand higher-level relations and concepts between words in a sentence or a paragraph.

Automatic EBM rule induction 303: Given the EBM database fields extracted from a medical journal, one uses secondary look-up tables to map drug names, diagnoses, and procedures onto NDC, ICD-9, CPT-4, and laboratory codes commonly used in claims-payment systems.

Human-Computer Interface (HCI) for human confirmation 305: The induced EBM rule along with the highlighted abstract is presented to a clinician for final confirmation with or without edit.

EBM population identification 307: One identifies potential control and intervention populations using the inclusion, exclusion, and trigger criteria. The presence or absence of the trigger criteria assigns a patient to the intervention or control group, respectively, provided that the patient satisfies the inclusion and exclusion criteria.

Dual-space clustering 309: This step creates meaningful consumer clusters that are homogeneous in the optimized baseline-period-attribute-and-outcomes (y) vector space. The baseline period equals the pre-intervention period of a fixed duration 1) For each EBM guideline, one builds models that predict various outcomes metrics. Associated with each predictive model is an optimal feature subset ($X \in R^N$, where N is the optimal feature dimension) derived from a combination of stochastic and combinatorial optimization algorithms.
2) In the vector space spanned by X, one performs clustering using k-means, expectation-maximization (EM), and Kohonen's self-organizing feature map algorithms. After clustering, there are $N_C$ clusters. For each cluster, one calculates the dispersion $\sigma_i$, i=1, ..., $N_C$ of each of the outcomes distributions and compare it with the overall dispersion $\sigma_T$ from the entire population. The dispersion-compression ratio (DCR) $r_i = \sigma_T/\sigma_i > \gamma$, where $\gamma > 1$, is a predetermined dispersion-compression threshold for accepting the $i^{th}$ cluster based on its ability to compress the outcomes distribution for more precision in applying EBM from an outcomes perspective. One creates a set of accepted samples for which clusters in X are sufficiently precise for performing integrated outcomes analysis. One selects the clustering algorithm that provides the highest DCR.
3) For the remaining population samples, perform feature optimization to derive a new optimal feature subset $X^{(k)}$. Compress $X^{(k)}$ into $X_c$ ($\dim(X_c) \ll \dim(X^{(k)})$) using linear discriminant analysis (LDA) and discretized outcomes metrics should they be continuous. Next, perform clustering in the vector space spanned by $X_c$ and y. Prior to clustering, normalize the vector space so that mean and standard deviation of each component will be 0 and 1, respectively. The standard deviation of y can be higher to reflect its importance in determining clusters. Keep the clusters whose DCRs>1.
4) For the remaining clusters, repeat step iii until the number of remaining samples is below the minimum threshold, i.e., (k)→(k+1). The final remaining samples represent the final cluster.

Integrated outcomes analysis 313: For each cluster, perform case-controlled impact analysis leveraging predictive and propensity-score models to account for both regression to the mean and selection bias. A comprehensive set of outcomes metrics encompasses both observed and inferred variables. For the inferred variables, we estimate individual and cluster prediction accuracies so that we can assess the level of statistical significance as a function of cluster size and model accuracy.

Figure 4:
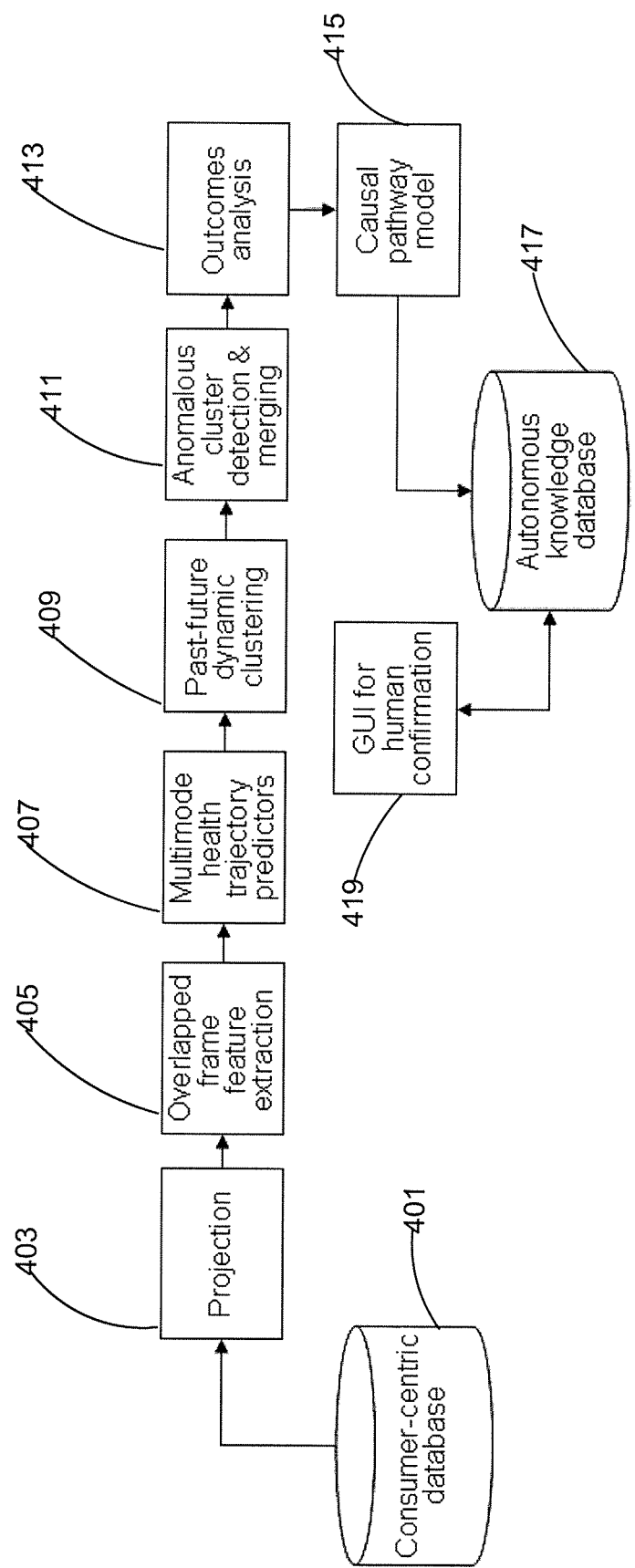
FIG. 4 shows a flowchart for an autonomous healthcare data exploration system in accordance with an embodiment of the invention.

Utility function generation 315: Finally we generate a set of utility functions.
1) Two-dimensional marginal utility functions over individual outcomes metrics and population clusters
2) One-dimensional utility function over a composite outcomes metric with weights
3) Pareto Frontier set for multiple outcomes metrics based on a user-defined multi-objective function Outputs of evidence-based-medicine supercharger 300 include:
Utility functions tailored to each stakeholder, a composite outcomes metric, or multi-objective optimization or Pareto-efficient plots
Outcomes metrics Autonomous Healthcare Data Exploration System FIG. 4 shows a flowchart for autonomous healthcare data exploration system 400 in accordance with an embodiment of the invention. Autonomous healthcare data exploration system 400 explores healthcare database to look for "interesting" relationships autonomously using various signal processing and data mining algorithms. There is often substantial hidden insight in healthcare data that can be discovered. Autonomous data exploration is sometimes associated with fraud detection. In healthcare, gaming or exploitation of loopholes in fee-reimbursement policies can be a serious problem, which has led to utilization management or medical necessity review by payers. For example, one study reports that 39% of physicians surveyed use at least one of the following three gaming methods:
1. Exaggerating the severity of patients' conditions
2. Changing patients' billing diagnoses
3. Reporting signs or symptoms that patients didn't have Fraud detection has been around for over two decades in a myriad of forms. It typically looks for outliers or uses models learned from labeled training data to identify suspicious activities for human confirmation. The two most widely used areas are in credit-card and financial industries. The U.S. Securities and Exchange Commission (SEC) and research boutique firms pore through tick-by-tick financial data to look for anomalous trading patterns that can signal insider trading.

Just to illustrate the difficulty of transitioning commercial antifraud solutions to healthcare, the U.S. Government Accountability Office reports that instead of adopting commercially available antifraud software to Medicare use, the Health Care Financing Administration (HCFA) chose to enter into a multi-year agreement with the Los Alamos National Laboratory, citing numerous difficulties with adopting commercial software. Unfortunately, no such software—commercial or custom-built—is in widespread use today.

The focus on fraud pits one stakeholder against another when outright fraud is relatively rare, and a soft form of exploiting system loopholes is more common in healthcare. Therefore, there is a need for a more sophisticated and less demeaning system focused on learning hidden causal relations between treatment and health outcomes (both positive and negative) so as to gain the widest possible acceptance from all the stakeholders.

FIG. 4 shows the flowchart of autonomous healthcare data exploration system 400, which leverages multimode health-trajectory predictors along with a consumer-centric database 401. Autonomous healthcare data exploration system 400 includes the following components:
Inputs
Consumer-centric database (CCDB) 401 consisting of membership, benefit-plan history, consumer-touch-point history, claims, self-reported, consumer behavior marketing, provider, and evidence-based medicine data
Autonomous knowledge database, which is empty in the beginning, but will be populated with new and iteratively refined knowledge Processing
Projection 403: This step creates multiple projections of CCDB 401 over time so that one has a complete view of all that's happening to each consumer conditioned upon slowly-changing lifestyle, behavior, and psychographic parameters.

Overlapped frame feature extraction 405: From each time frame of each projection space, one extracts an appropriate number of summarization and dynamic features so that we can track their trajectories over time.

Multimode health-trajectory predictors 407: Predictors 407 predict future states of one's health around disease progression, engagement, and impact.

Past-future dynamic clustering 409: Clustering is performed on the vector space spanned by the current set of features and predicted attributes. In one embodiment of such a system, the current set of features encompasses the parameterization of current disease conditions, utilization of medical resources, and lifestyle/health behavior. Predicted attributes may include disease progression, the level of impactability, and future cost. The key idea is to cluster consumers based on both where they are today and where they are likely to transition to in the future.

Anomalous cluster detection and merging 411: Within each homogeneous cluster, one looks for outliers in joint and marginal spaces. Depending on the outlier-population size derived from each cluster, one merges outliers from multiple similar clusters to improve statistical power and significance.

Outcomes analysis 413: For each outlier cluster, one looks for attributes with commonality and differences between outliers and normal cases. This search for common and uncommon attributes facilitates case-controlled outcomes analysis with drilldown along with the understanding of factors responsible for differences in outcomes.

Causal pathway analysis 415: For each anomaly case identified, one uses a structural learning algorithm to induce a Bayesian network structure. Next, one ensures that causal parameters between control and test groups move in a logical way.

GUI for human confirmation 419: Each discovered knowledge is presented to a human expert for final confirmation and inclusion into the autonomous knowledge discovery database 417.

Figure 5:
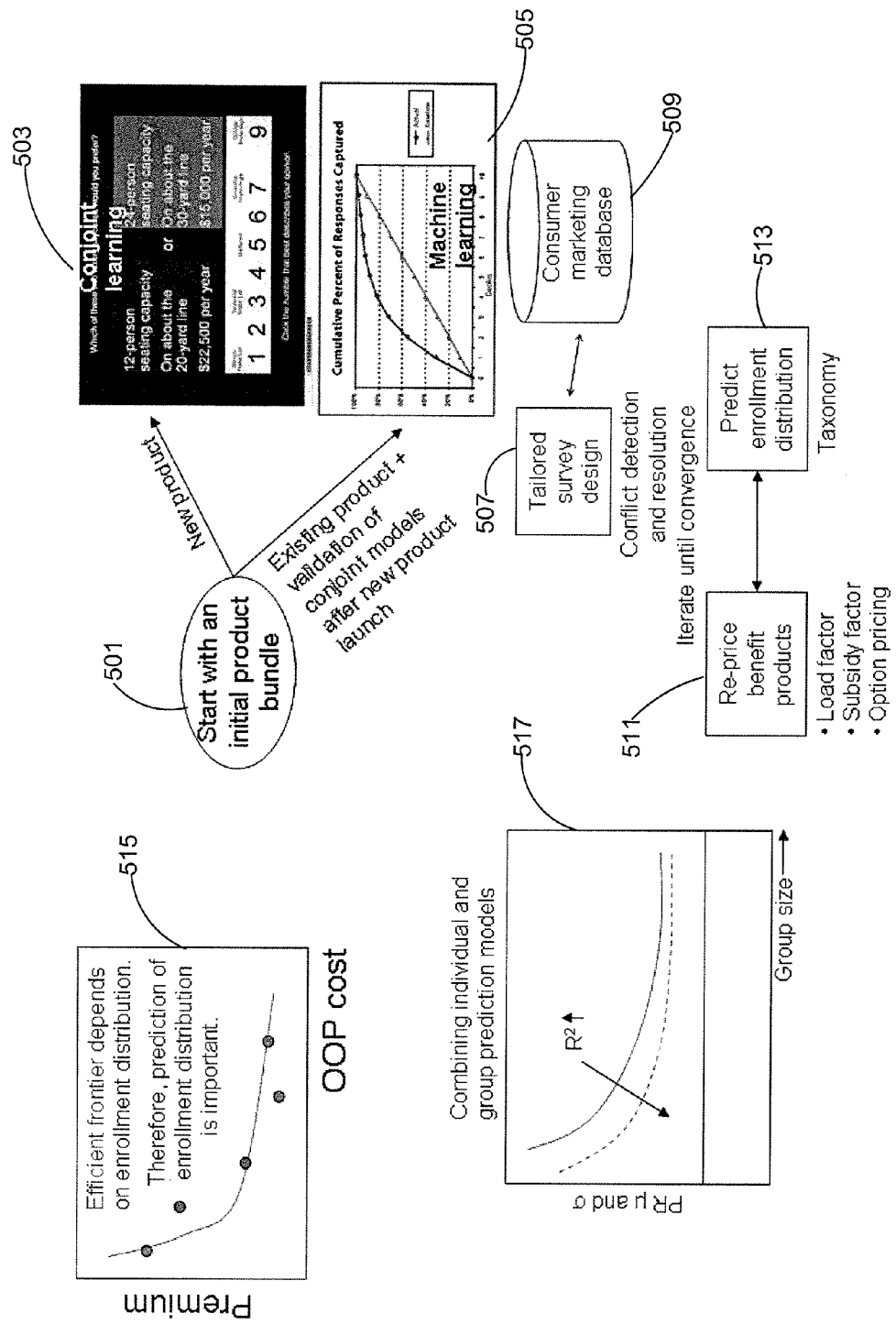
FIG. 5 shows an illustrative conceptual example of the optimal health benefit design in accordance with an embodiment of the invention.

Outputs provided by autonomous healthcare data exploration system 400 include:
Extracted knowledge Intelligent Health Benefit Design System FIG. 5 shows an illustrative conceptual example of the optimal health benefit design in accordance with an embodiment of the invention. An intelligent benefit design system leverages ideas from consumer-understanding technologies, predictive modeling, impact analysis, and multi-objective optimization to design an individually tailored benefit product that balances the conflicting needs of moral hazard and social insurance by finding the acceptable ratio of profitability to subsidization for each product or plan configuration in a product bundle.

Element 515 in FIG. 5 shows a simplified two-dimensional efficient frontier in the two-dimensional space of premium and out-of-pocket (OOP) cost with an indifference curve. That is, higher premiums are generally associated with lower OOP costs and vice versa. An insurance company starts out with an initial set of product bundles 501. If the company introduces a new product for which no prior enrollment data is available, then the product enrollment distribution is estimated using adaptive conjoint learning and prediction 503. On the other hand, if product changes are evolutionary, then one can use prior enrollment data to develop and deploy predictive models to estimate the new product enrollment distribution given an initial set of product attributes 505. As part of designing an adaptive conjoint analysis (ACA) questionnaire, one leverages consumer marketing database or demographic database from the U.S. Census Bureau so that the questionnaire can be tailored to each consumer 507, 509.

The fundamental idea is to iterate the process of adjusting product attributes, estimating product enrollment distributions, and calculating economic parameters (projected profit/loss as well as the level of subsidization inherent in a medical insurance product) of each product bundle so that we achieve an acceptable trade off between social insurance and moral hazard. That is, while the young and healthy are supposed to subsidize the cost of insurance for the old and sick, there needs to be an element of personal responsibility in benefit design so that people with poor health habits and beneficiary mentality do not abuse the entire healthcare system to the detriment of all 511, 513. In short, benefit design must deal effectively with risk factors that can be mitigated within socially acceptable means. The plot labeled 517 shows the relationship between individual prediction accuracy measured in R-sq or $R^2$ and group prediction accuracy measured in predictive ratio (PR) mean ($\mu$) and standard deviation ($\sigma$). Individual predictive accuracy becomes less important as group size increases as in employer or group underwriting. However, in clinical settings and predicting benefit enrollment, where adverse selection can occur frequently, individual predictive accuracy is of paramount importance.

In healthcare, benefit design, according to prior art, is typically carried out by linking historical utilization and cost data to various benefit parameters, such as co-pay, deductible, co-insurance, maximum out-of-pocket, limits on Health Savings Account/Flexible Spending Account (HSA/FSA), etc. Then a loading factor (margin) is computed for each plan design, which sets the premium for the plan. Depending on the premium differential between plans, subsidization factors are calculated such that a plan attractive to predominantly the healthy (high-deductible plans) may subsidize the cost of another plan that appeals primarily to the sick so that the concept of social insurance can be preserved in plan design.

An important consideration in benefit design is risk management. If benefit parameters are particularly attractive to a certain segment of population whose medical needs differ significantly from those of the general population, then such a plan has a high likelihood of attracting a biased population, which can lead to unexpected profit or loss depending on the direction of the bias. Unfortunately for health insurance companies, this phenomenon of biased population (called anti- or adverse selection) is not uncommon. The result is a cookie-cutter benefit design with a small number of selections so that the law of large numbers dominates the field.

More recently under the banner of consumer-directed health plan (CDHP), many payers started introducing high-deductible, low-premium plans. The theory of the case for CDHP is that high-deductible plans with some form of medical savings account will turn beneficiary-mentality patients into sophisticated healthcare consumers. Unlike other consumer industries, healthcare consumers may have hard time correlating actual high-quality care with a perceived one of at least based on RAND's quality metrics. Furthermore, the initial thrust of CDHP was to attract the cream-of-the-crop population from employers offering plans from multiple payers. That is, nimble new-to-the-market payers introduced CDHP products to employers desperate to cut soaring health benefit costs. The end result was that dinosaur payers were saddled with the undesirable segment of the population, hurting their bottom line.

Studies suggest that while the young and healthy are potential winners of CDHP, their opportunities for savings are limited because of restrictions in plan design, such as portability and investment. Results of post-CDHP health-resource utilizations and costs suggest mixed results with no clear trend. Perhaps mixed results are not surprising given the ambiguity of the theory of the case.

Perhaps the biggest shortcoming of the current health plan design is that few incorporate innovative design parameters, such as consumer-engagement strategies, incentives for lifestyle changes, and fun aspects in linking validated evidence-based-medicine guidelines, nutrition and exercise to health. Our design approach leverages the estimation of a consumer-preference function and projected utility functions derived from the impact analysis engine to move away from a cookie-cutter design and towards a tailored plan design that impacts health behavior change.

For new product launch 501, one first proceeds with adaptive conjoint questionnaire (ACQ) 503 that is designed to minimize the number of questions leveraging predictive questionnaire construction. From ACQ responses, one can estimate a consumer preference function at an individual level. From a pool of initial product bundles with preset features, one estimates the overall enrollment distribution for a group (i.e., an employer). From the overall enrollment distribution and the outputs of multimode health-trajectory predictors, one computes profit/loss for each product and generate a three-dimensional picture of profit/loss and compressed two-dimensional objectives (i.e., minimize premium and out-of-pocket or OOP expense) as shown in relationships 515 and 517. This picture will provide visual insights to facilitate the understanding of Pareto-efficient design parameters, which can lead to the reconfiguration of product features. This process of enrollment prediction and product reconfiguration is iterative until the incremental change in product-feature reconfiguration is below an acceptable threshold.

After the product launch, one starts with a fresh data set, which represents the actual product selection behavior by consumers. Unlike in conjoint analysis, one does not have information on exactly which products consumers traded off before making product-selection decisions. One has the following information on consumers and their product-selection behavior:

1. Demographics and behavior marketing ($x_{demo}$, $x_{cbm}$)
2. Prior product selection ($x_{pps}$), which doesn't exist for new consumers
3. Current product selection The task at hand is to estimate a revised consumer preference function using real data. Let y and w denote the product-selection behavior and product features, respectively. Then, the estimation task is as follows:

$$\hat{y}=f(x_{demo},x_{cbm},x_{pps},w,D(w,y)),$$

where $D(w,y)$ is a distance function between w and y, and $f(\bullet)$ can be estimated using parametric or nonparametric learning algorithms. Any differences between the conjoint and real-data models are stored in a database for continuous model adaptation and learning. More complex design with incentives requires utility functions associated with incentives from the impact-analysis engine. After estimating the consumer-preference function, there is a secondary step of identifying intervention opportunities given the characteristics of consumers choosing each product bundle. Based on utility functions and the outputs of the multimode health-trajectory predictors, the remaining task is to design an incentive program within each product bundle that will encourage high-risk members to participate in the program.

Figure 6:
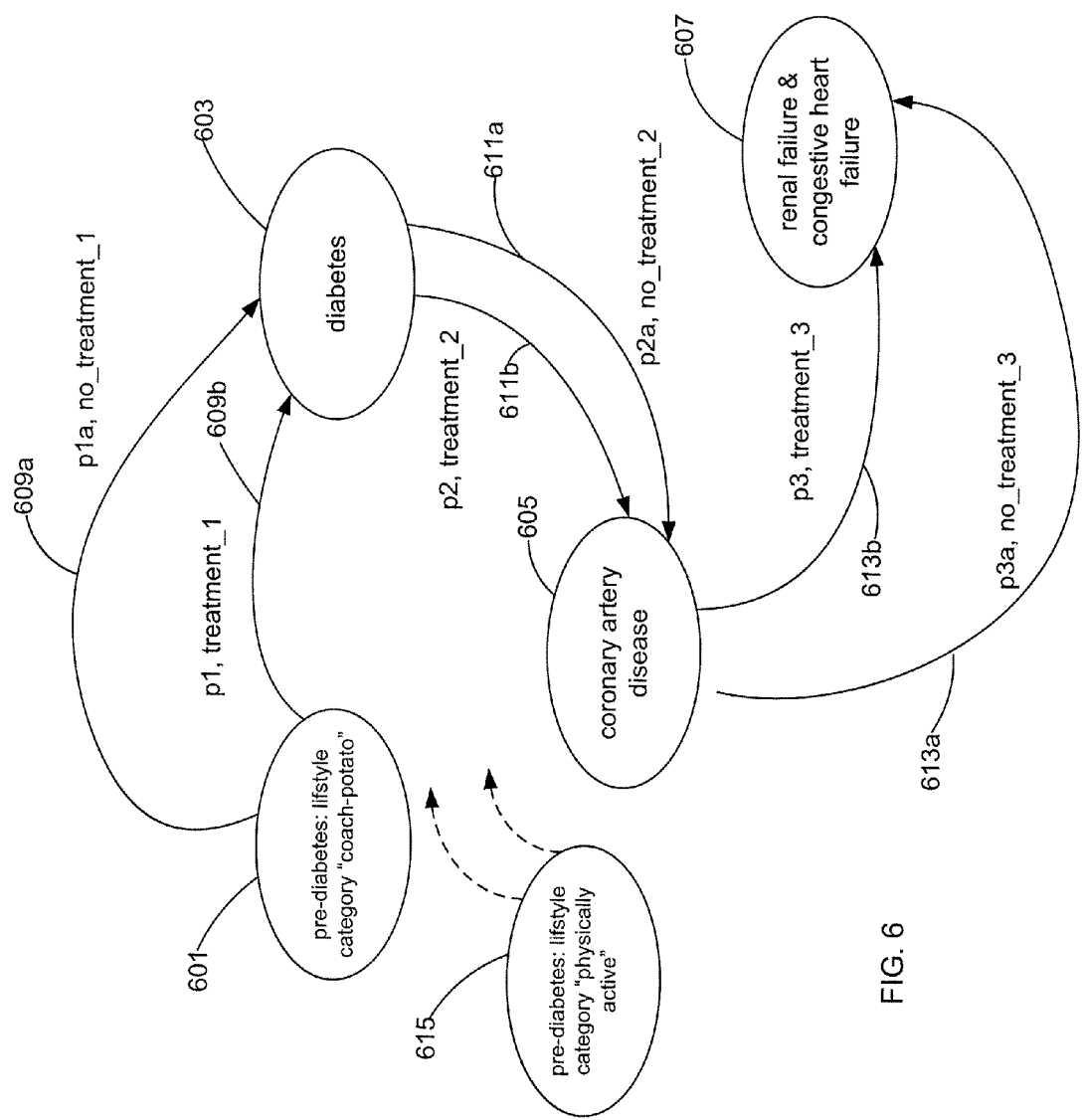
FIG. 6 shows an example of Markov modeling of assessing a target of opportunity in accordance with an embodiment of the invention.

FIG. 6 shows an example of Markov modeling of assessing a target of opportunity in accordance with an embodiment of the invention. Markov model 600 shows a disease progression related to diabetes. Markov model 600 shows the probability of transitioning from one disease state to another disease state based on whether the consumer obtains a prescribed treatment. Additionally, disease states may depend on observed behavioral/lifestyle factors including the attributes of the consumer. Attributes may include the category of life style (e.g., "coach-potato") and level of education of the consumer. The type of treatment and the efficacy of the treatment may depend on the consumer's attributes.

With state 601, a consumer, who is a "couch-potato," is determined to be a pre-diabetic. As determined by intervention opportunity finder 103 (as shown in FIG. 1), there is a probability $p_{1_a}$ 609a of the consumer becoming a diabetic (state 603) without any treatment and a probability $p_1$ 609b if the consumer received a prescribed treatment (treatment_1). For example, EBM supercharger 300 may determine that the consumer can substantially reduce the probability of becoming a diabetic with a proper diet and exercise regime under the supervision of a dietician and/or exercise coach.

When the consumer becomes a diabetic, there is a probability of developing coronary artery disease (corresponding to state 605). The corresponding treatment_2 (as determined by EBM supercharger) may be more radical than treatment_1. For example, treament_1 may include one or more prescribed drugs that are typically more costly than providing a dietician and/or exercise coach. (In general, as a disease progresses, the associated costs increase.) The probability of a diabetic developing coronary arterial disease without treatment is $p_{2_a}$ 611a and $p_2$ 611b with treatment.

In accordance with Markov model 600, once a consumer has developed coronary arterial disease, the consumer may further develop renal failure and/or congestive heart failure (state 607). The probability of developing renal failure/congestive failure is $p_{3_a}$ 113a without treatment is and $p_3$ 611b with treatment.

Markov model 600 may include states based on different attributes of a consumer. For example, state 615 is associated with the consumer having a physically active life style.

Consequently, the transition probability of disease progression is typically smaller than a consumer having has a sedentary lifestyle (corresponding to state 601, in which a consumer is classified as a "coach-potato).

Exemplary Scenario

Sarah is a 45-year-old mother of two children, overweight, pre-diabetic, being treated for hypertension and hyperlipidemia. At work, she needs to enroll in a health benefit plan since her employer switched to a new payer, Global Health. In accordance with an embodiment of the invention, the following scenario that a consumer experiences.

Enrollment: Sarah is first given a combination of Predictive Health Risk Assessment (PHRA) interspersed with Adaptive Conjoint Analysis (ACA) questions. Even without single claims, PHRA calculates future health trajectories and guides Sarah through the benefit selection process based on an adaptive questionnaire tree designed to minimize the number of questions while maximizing predictive accuracy. She ends up selecting an HMO plan with various incentives for staying healthy. Impact analysis engine provided ROI's associated with incentives for consumers who fit Sarah's profile. She is given an instant analysis of her current health, likely health trajectories, and what she can do to prevent unpleasant outcomes. An interactive goal setting wraps up her first-day consumer experience with GH. Health trajectory predictors are based on PHRA/ACA questions, in which the optimal benefit design is part of resource allocation management (RAM). (With prior art, Sarah is typically given a list of traditional HMO, PPO, and Indemnity plans with a limited number of choices in deductibles, co-pays, and premium with health savings accounts.)

At-risk member identification: By virtue of PHRA, Sarah has already been identified as an at-risk member who can benefit from intervention. PHRA lists diabetes as a major risk factor given her current conditions, BMI, and lifestyle parameters inferred from external consumer behavior data obtained from Experian for a specific purpose of improving health guidance, not premium setting. Given her status, she gets a VAT call tailored to her situation, along with a two-page feedback/action plan letter based on her responses to the PHRA questionnaire all during the first week as part of a welcoming package. The Integrated Health Management Platform supports this function with health trajectory predictors, intervention opportunity finder; and RAM. (With prior art, since Sarah is a new member, GH must wait for claims data to accumulate before running a predictive model that predicts 12-month future cost. Because of claims lag, the typical wait time is 6 months.)

Maintenance: Based on earlier communications, Sarah understands what to do. She takes PHRA frequently to report her progress and to see if her health scores are improving. Upon meeting her first goal of losing 10 lbs in 4 weeks and improving her health scores by 10%, GH sends her a USB pedometer. Now she uses it to keep track of her activity level daily, uploading to her personal Web portal at GH activity data, which provides additional data points to the IHM Platform in order to improve guidance for Sarah. Meanwhile the IHM Platform is exploring healthcare database autonomously, looking for patterns that precede low-to-high or high-to-low transitions so that it can update its knowledge database. Furthermore, it is constantly monitoring the relationship between intervention and outcomes to ensure that every member gets the best possible touch points to maximize population health using both high-tech and human interventions. The multimode health-trajectory predictors perform predictions both on a regular basis and asynchronously (event-driven). All IHM components work seamlessly to make this happen. (With prior art, not knowing the full extent of her risk factors, she may live her life as she normally does. One day, she feels chest pain and goes to ER. Upon examination, they find out that she needs heart bypass. Further blood test shows her blood glucose level at 175 mg/dl, which makes her a diabetic, further complicating her recovery. About 3 months after her bypass surgery, GH finally has her claims data in an electronic data warehouse. The indigenous PM now flags her as a high-risk member—a clear case of regression to the mean and fixing the door after a cow has already left. A nurse calls her to inquire if anything can be done to help her.)

Computer Implementation

Figure 7:
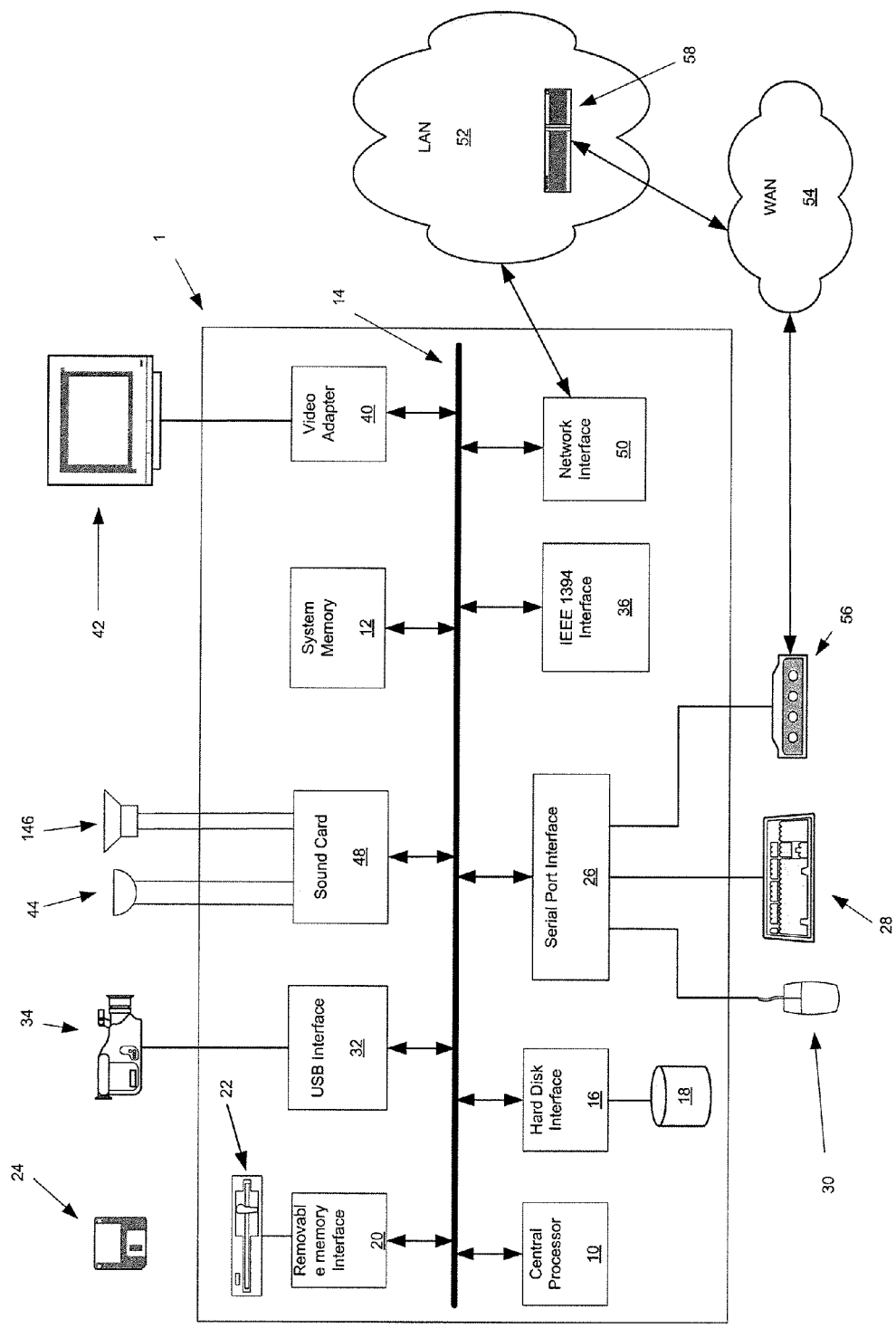
FIG. 7 shows computer system 100 that supports an embodiment of the invention.

FIG. 7 shows computer system 1 that supports an integrated health management platform (e.g., IHM platform 100 as shown in FIG. 1) in accordance with an embodiment of the invention. Elements of the present invention may be implemented with computer systems, such as the system 1. Computer system 1 includes a central processor 10, a system memory 12 and a system bus 14 that couples various system components including the system memory 12 to the central processor unit 10. System bus 14 may be any of several types of bus structures including a memory bus or memory controller, a peripheral bus, and a local bus using any of a variety of bus architectures. The structure of system memory 12 is well known to those skilled in the art and may include a basic input/output system (BIOS) stored in a read only memory (ROM) and one or more program modules such as operating systems, application programs and program data stored in random access memory (RAM).

Computer 1 may also include a variety of interface units and drives for reading and writing data. In particular, computer 1 includes a hard disk interface 16 and a removable memory interface 20 respectively coupling a hard disk drive 18 and a removable memory drive 22 to system bus 14. Examples of removable memory drives include magnetic disk drives and optical disk drives. The drives and their associated computer-readable media, such as a floppy disk 24 provide nonvolatile storage of computer readable instructions, data structures, program modules and other data for computer 1. A single hard disk drive 18 and a single removable memory drive 22 are shown for illustration purposes only and with the understanding that computer 1 may include several of such drives. Furthermore, computer 1 may include drives for interfacing with other types of computer readable media.

A user can interact with computer 1 with a variety of input devices. FIG. 7 shows a serial port interface 26 coupling a keyboard 28 and a pointing device 30 to system bus 14. Pointing device 28 may be implemented with a mouse, track ball, pen device, or similar device. Of course one or more other input devices (not shown) such as a joystick, game pad, satellite dish, scanner, touch sensitive screen or the like may be connected to computer 1.

Computer 1 may include additional interfaces for connecting devices to system bus 14. FIG. 7 shows a universal serial bus (USB) interface 32 coupling a video or digital camera 34 to system bus 14. An IEEE 1394 interface 36 may be used to couple additional devices to computer 1. Furthermore, interface 36 may configured to operate with particular manufacture interfaces such as FireWire developed by Apple Computer and i.Link developed by Sony. Input devices may also be coupled to system bus 114 through a parallel port, a game port, a PCI board or any other interface used to couple and input device to a computer.

Computer 1 also includes a video adapter 40 coupling a display device 42 to system bus 14. Display device 42 may include a cathode ray tube (CRT), liquid crystal display (LCD), field emission display (FED), plasma display or any other device that produces an image that is viewable by the user. Additional output devices, such as a printing device (not shown), may be connected to computer 1.

Sound can be recorded and reproduced with a microphone 44 and a speaker 66. A sound card 48 may be used to couple microphone 44 and speaker 46 to system bus 14. One skilled in the art will appreciate that the device connections shown in FIG. 7 are for illustration purposes only and that several of the peripheral devices could be coupled to system bus 14 via alternative interfaces. For example, video camera 34 could be connected to IEEE 1394 interface 36 and pointing device 30 could be connected to USB interface 32.

Computer 1 can operate in a networked environment using logical connections to one or more remote computers or other devices, such as a server, a router, a network personal computer, a peer device or other common network node, a wireless telephone or wireless personal digital assistant. Computer 1 includes a network interface 50 that couples system bus 14 to a local area network (LAN) 52. Networking environments are commonplace in offices, enterprise-wide computer networks and home computer systems.

A wide area network (WAN) 54, such as the Internet, can also be accessed by computer 1. FIG. 7 shows a modem unit 56 connected to serial port interface 26 and to WAN 54. Modem unit 56 may be located within or external to computer 1 and may be any type of conventional modem such as a cable modem or a satellite modem. LAN 52 may also be used to connect to WAN 54. FIG. 7 shows a router 58 that may connect LAN 52 to WAN 54 in a conventional manner.

It will be appreciated that the network connections shown are exemplary and other ways of establishing a communications link between the computers can be used. The existence of any of various well-known protocols, such as TCP/IP, Frame Relay, Ethernet, FTP, HTTP and the like, is presumed, and computer 1 can be operated in a client-server configuration to permit a user to retrieve web pages from a web-based server. Furthermore, any of various conventional web browsers can be used to display and manipulate data on web pages.

The operation of computer 1 can be controlled by a variety of different program modules. Examples of program modules are routines, programs, objects, components, and data structures that perform particular tasks or implement particular abstract data types. The present invention may also be practiced with other computer system configurations, including hand-held devices, multiprocessor systems, microprocessor-based or programmable consumer electronics, network PCS, minicomputers, mainframe computers, personal digital assistants and the like. Furthermore, the invention may also be practiced in distributed computing environments where tasks are performed by remote processing devices that are linked through a communications network. In a distributed computing environment, program modules may be located in both local and remote memory storage devices.

In an embodiment of the invention, central processor unit 10 determines health trajectory predictors from HRA data 151, claims data 153, and CBM data 155 (as shown in FIG. 1), which are obtained through LAN 152 and WAN 154. Central processor unit 10 may also provide the functionalities of intervention opportunity finder 103, resource allocation manager 105, and impact analysis engine 107. Consequently, central processor unit 10 may provide a target of opportunity for a consumer from evidence-based medicine (EBM) guidelines or medical journals 351 (as shown in FIG. 351). EBM guidelines (corresponding to EBM database 317) and electronic health records (EHR) (corresponding to EHR database 203) may be retrieved from hard disk drive 18.

As can be appreciated by one skilled in the art, a computer system with an associated computer-readable medium containing instructions for controlling the computer system may be utilized to implement the exemplary embodiments that are disclosed herein. The computer system may include at least one computer such as a microprocessor, a cluster of microprocessors, a mainframe, and networked workstations.

Architecture for Supporting MPRPLR Health Games

Embodiments of the invention combine fun and excitement in the context of health and wellness. Online personalities and behaviors may mimic the real world to create a tunnel between the real and virtual worlds, where a participant's (user's) real-world activities are reflected on how well the participant performs in the virtual world, governed by advanced analytics engines. While risk-taking behaviors in the online world may be more daring than in the real world, it is possible to link real-world behaviors to virtual-world behaviors in an attempt to be more precise in targeting lifestyle-based rewards to a much faster-paced online world. Exemplary benefits are as follows:

1. Causal relations between lifestyle choices and health outcomes can be taught in a more entertaining manner in the virtual world.
2. Progress and outcomes can be measured in an accelerated pace during an immersive gaming experience as part of push and pull between inferred consumer traits from sensor data and translating them into gaming parameters to teach the consequences of lifestyle choices in a highly tailored mode.
3. Feedback can be tailored and subtle, unlike blatantly obvious and ineffective messages from traditional health Web sites, such as "You need to eat five servings of fruits and vegetables." In the virtual world, the consumer's alter ego may need to take deficient nutrients in order to regain full strength and fight seemingly invincible enemies.

Embodiments of the invention support the following characteristics that may be lacking in prior art health games:

Fun and excitement: There is not too much fun to learn what you already know expressed in dry clinical language with a misguided sense of precision in certain instances.

Progress and outcomes measured in real time: In health, everything moves in a glacial pace. Not being able to measure progress leads many to give up and wander aimlessly.

Feedback: Most healthcare portals tell what is obvious. For example, yourdiseaserisk (available at http://www.yourdiseaserisk.harvard.edu/) offers the following feedback after the consumer fills out a questionnaire to assess his risk for osteoporosis, which represents a straight regurgitation of one's responses to the osteoporosis risk-assessment questions:

You get too much vitamin A.
You don't smoke cigarettes.
You are physically active for at least 30 minutes a day.
You are not underweight.
You eat green leafy vegetables on most days.
You take a vitamin D or multivitamin supplement.

Figure 8:
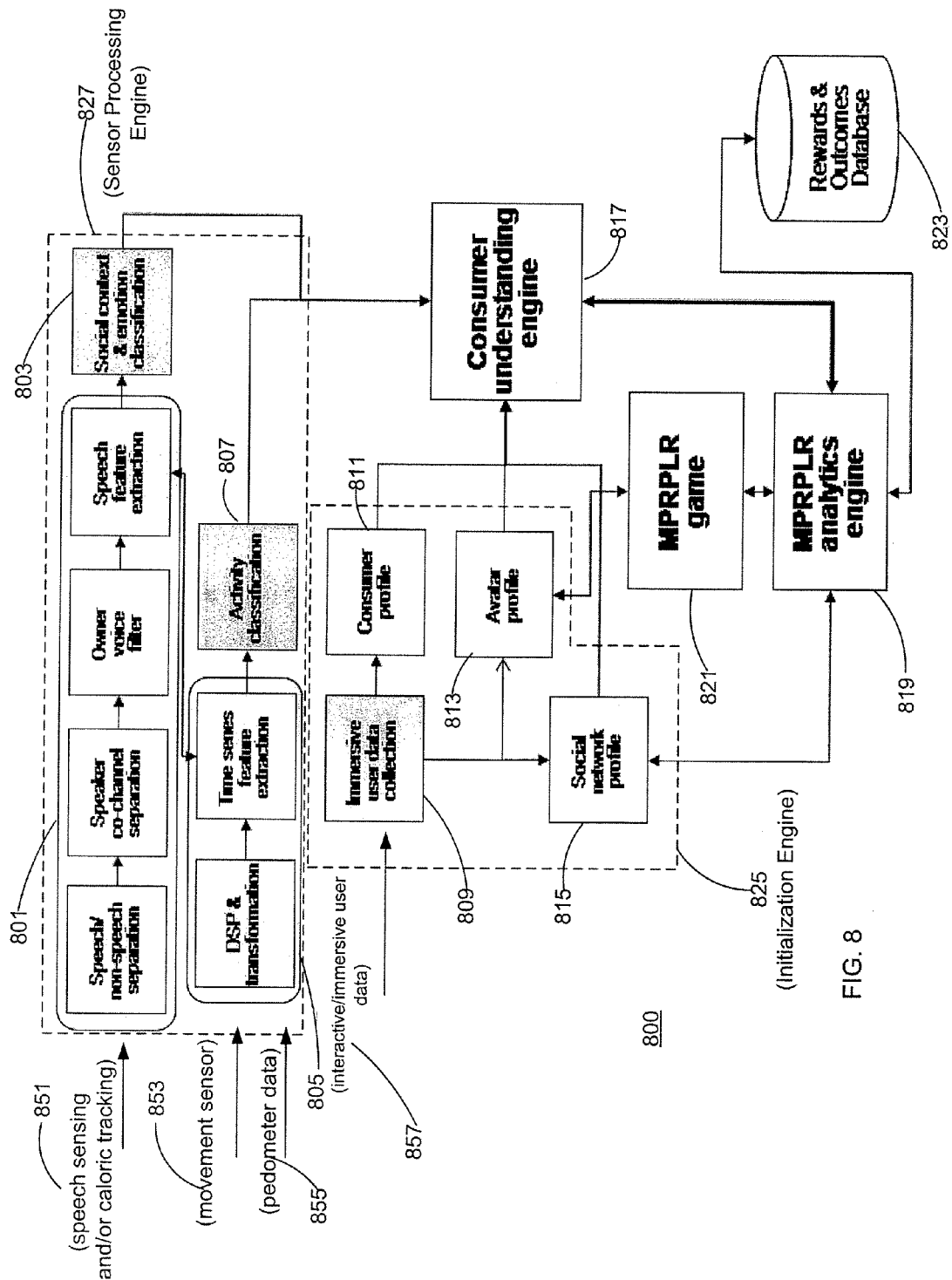
FIG. 8 shows a multi-player, role-playing, lifestyle-reward (MPRPLR) architecture in accordance with an embodiment of the invention.

FIG. 8 shows multi-player, role-playing, lifestyle-reward (MPRPLR) architecture 800 in accordance with an embodiment of the invention. As will be appreciated by those skilled in the art upon review of this disclosure, different embodiments of MPRPLRs may utilize various forms of computer systems and transmission systems. As one example, one embodiment may utilize computer system 1 as shown in FIG. 7 for implementing at least part of architecture 800. Embodiments of the invention are directed towards enhancing a participant's health by motivating the participant to change lifestyle voluntarily and happily. As provided in exemplary architecture 800, a participant wears or is in operative communication with a health device that can measure calories expended and/or sense speech to collect speech sensing/caloric tracking data 851. Data 851 may be collected with one sensor performing both speech sensing and calorie tracking or with two sensors each performing separate functions. Calorie tracking may be determined by tracking body movements continuously using a watch-like device or a sensor embedded in shoes or in combination. In this context, calorie tracking is possible by estimating calorie expenditure over time.

Activity measurement may be performed using a 2-axis accelerometer to collect movement data 853 while a separate calibration engine may translate activity levels into caloric expenditure over time. The level of activities may be measured using an embedded or wearable sensor, such as a pedometer that can transmit pedometer data 855 wirelessly to a receiver or store data on a resident memory device for later retrieval. Speech sensing data 851, which is typically significant important for understanding the social context of the consumer's daily activities, is processed by speech module 801.

Incoming sensor signals 853 and 855 are processed through a bank of preprocessing module 805 to produce a higher-level-of-abstraction data through the use of semi-supervised learning algorithms that encompass active learning. Advanced analytics working on real-time data collected from health sensors and immersive gaming convert noisy raw data into insights on the consumer's daily activities, social context, and emotional states.

Immersive user (participant) data collection 809 accomplishes what traditional health questionnaires typically cannot accomplish. Instead of bombarding the consumer with a number of mundane questions, the immersive gaming environment allows the consumer to create an avatar and subject the avatar (corresponding to avatar profile 813) to a number of situations in which it has to make trade-off decisions from which the algorithm can derive consumer profiles 811. (An avatar is an embodiment of a quality or concept; an archetype.) This approach is conceptually analogous to ethnographic research except all the trade-off decisions take place in a virtual world mimicking the real world in which the consumer lives. Further, immersive user data is likely to be more accurate and less subjective than requiring a user to estimate or quantify physical, emotional, and/or social characteristics.

Consumer understanding engine (CUE) 817 and MPRPLR analytics engine (MAE) 819, which are two advanced analytics engines, work in synergy to reflect the consumer's real-world parameters into the virtual world. CUE 817 establishes the consumer's value hierarchy, desired aspirations by noting the similarities, and differences between the real person and the virtual representation in the form of an avatar, and other relevant profiles inferred based on trade-off decisions and the outputs of active learning algorithms. MA engine 819 manipulates the virtual world so that good health behaviors are rewarded in the virtual gaming world while showing the predicted path as the game progresses so that the causality between real-world health behavior and virtual-world outcomes can be ingrained in the consumer's brain.

Exemplary architecture 800 includes the following components:

Inputs
  Speech-sensing data 851: Module 801 may be configured to not store speech data 851 in order to alleviate privacy concerns. Instead, module 801 may internally process speech snippets and store information related to social context and emotional attributes throughout the day while the device is on or otherwise in communication with the body.

Calorie-tracking: Module 805 keeps track of calories expended using a two-axis accelerometer or a simple pedometer from motion sensing data 853 and pedometer data 855.

Immersive user data 857: In an immersive online gaming environment, the consumer is confronted with fun tasks where he must make decisions to proceed forward. Immersive user data collection module 809 processes user-contributed data (immersive user data) 857, in which decision points along with environmental cues are stored for real-time analysis.

Rewards & outcomes database 823: Rewards & outcomes database (RODB) 823 is initially populated with default values extracted from relevant literature and research reports. The default values will get refined over time as the system collects more interaction data between the system and the consumer.

Processing

Speech processing module 801: Speech processing encompasses (1) speech/non-speech separation, (2) speaker co-channel separation so that we can identify and separate multiple speakers the participant comes in contact with as a function of time, (3) filtering of the participant's voice, and (4) feature extraction so that the learning algorithm can understand the social and emotional context of the participant throughout the day.

Sensor signal processing module 805: The activity data collected by a wireless pedometer or a 2-axis accelerometer are processed through digital signal processing (DSP) and projection algorithms from which a set of features is extracted to determine the type of activities (running, walking, stationary, etc.) as a function of time. Both time-series and speech features can be used to improve the overall classification accuracy.

Immersive user data collection module 809: This module provides an immersive gaming experience coupled with decision making. The decisions the participant makes throughout this virtual-world registration process are more realistic and accurate than asking intrusive personal questions during a typical survey-based information-gathering process.

Classification may include the following functionalities:

1) Affect classification: Module 803 leverages speech and activity features, in which an affect learning algorithm estimates affective states of the participant periodically.

2) Characterization of social encounters: Module 803 characterizes social encounters in terms of the number of people in contact, duration, frequency, and affective states during encounters as a function of the number of people the participant comes in contact with.

3) Activity recognition: Module 807 leverages the outputs of pedometers and/or calorie trackers to provide an index of daily activities as a function of time.

Participant profile 811: The social and action environments during the immersive game-based registration are encoded using an (Extendable Markup Language) XML-based ontology. All the decisions made by the participant are entered into an XML template that aligns all the decision points with trade-off choices in the context of prevailing social and action conditions. For instance, if the participant prefers money over health at one of the forks in the road, then system 800 can assume certain characteristics about his motivational hierarchy in designing a reward system tailored to the participant. For example, instead of touting the health benefits of working out, system 800 can point out to a research study that shows that an elderly couple with a company-sponsored health insurance is still expected to spend $200K in out-of-pocket costs and that living healthy not only improves one's quality of living, but also reduces unnecessary medical costs substantially.

Avatar profile 813: Based on the way the participant constructs his avatar, system 800 can glean insights into the participant's alter ego, which may represent the kind of person the participant wants to be or known for to the outside world.

Social-network profile 815: During the immersive gaming as part of the registration process, system 800 can note the type of social activities the participant participates in as part of problem solving and decision making.

Consumer-understanding engine (CUE) 817: CUE 817 generates a comprehensive participant stimuli-response model with a stochastic utility model. The basic idea is to get inside the mind of the participant by taking into account the participant's value hierarchy, cognitive skills, behavioral traits, collaborative filtering (CF) parameters, linkage between emotion and action, social interactions, and psychographic parameters.

MPRPLR analytics engine 819: Engine 819 performs a detailed data analysis of how the participant interacts with the physical and social environments in the pursuit of a set of specific goals tailored to the participant based on recommendations from the CUE.

MPRPLR game module 821: Game module 821 may be highly tailored to report lifestyle data as interpreted by the two engines. The objective of the game is to create a virtual environment, where community members can engage in exciting adventures and pursue meaningful relationships subject to constraints imposed by real-life activities.

Outputs

Reward and feedback parameters associated with the MPRPLR game: All the available rewards may be parameterized and doled out to the participants in the virtual world. The amount, type, and frequency of rewards may be determined based on the utility function estimated from the projected performance differences exhibited by a user (participant) before and after the rewards. The actual algorithm will be a combination of predictive models and population normalization algorithms using propensity scores.

Figure 9:
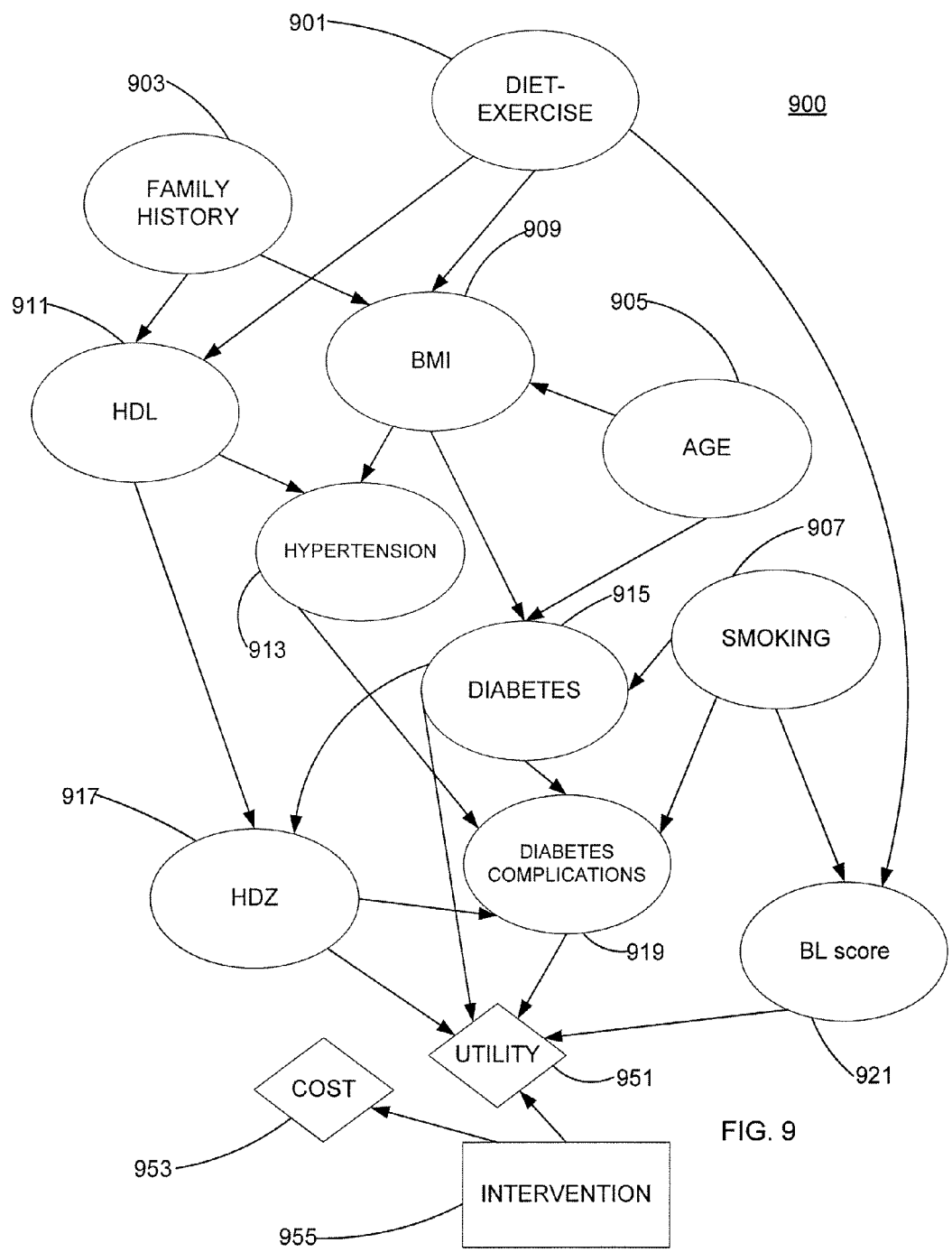
FIG. 9 shows a causal network with utility, action, and cost nodes for an allocation of available resources in accordance with an embodiment of the invention.

Utility functions associated with reward parameters and subsequent health outcomes: FIG. 9 shows an example from the chronically ill population suffering from diabetes, heart disease, and/or diabetic complications. The intervention node is equivalent to decision points subject to cost-benefit analysis. The key advantage stems from knowing the relationship between intervention (reward) and health outcomes as a function of modifiable risk factors.

FIG. 9 shows causal network 900 with utility (outcomes) node 951, action (intervention) node 955, and cost node 953 for an allocation of available resources in accordance with an embodiment of the invention. Causal network 900 provides for judicious allocation of available resources to enhance benefits to participants based on attributes of the participants. As shown in causal network 900, system 800 obtains information about health factors (characteristics) of the participant, including, for example, diet-exercise 901, family history 903, age 905, smoking 907, and body mass index (BMI) 909. Health characteristics may affect other health factors (health conditions), including low-density lipoprotein (LDL) measure 911, and hypertension 913, which may further lead to other health conditions (illnesses) including diabetes 915, HDZ (heart disease) 917, and diabetes complications 919. BL behavior/lifestyle score 921 predicts the health and projected health of the participant. (As previously discussed, as shown in FIG. 1, health trajectory predictor module 101 tracks the progression of an illness as exemplified in FIG. 6.)

System 800 obtains information about a participant, causing propagation through causal network 900 to change the beliefs about the other unknown participant attributes (inference). Health attributes 901-907 may affect health factors. For example, the participant may be characterized as a "couch-potato" (corresponding diet-exercise 901 with a high fat diet and little exercise), causing BMI factor 909 to increase. As shown in causal network 900, BMI factor 909 in conjunction with Age factor 905 is conducive to diabetes illness 915 and eventually to diabetes complications 919.

From intervention node 955, utility node 951, and cost node 953, system 800 can determine the cost-benefit relationship of an appropriate intervention (e.g., treatment) to address the state of health of the participant. (As previously discussed, as shown in FIG. 1, intervention opportunity finder module 103 may find a treatment based on an impact assessment.) For example, the participant may suffer from hypertension 913 and smoking 907 but does not yet suffer from diabetes 915. System 800 consequently determines that it highly beneficial to encourage the participant to stop smoking. If the participant reduces smoking one pack rather than three packs of cigarettes, system 800 may reward the participant by enabling the participant's virtual character to better combat the opposition.

Exemplary Scenario

Figure 10:
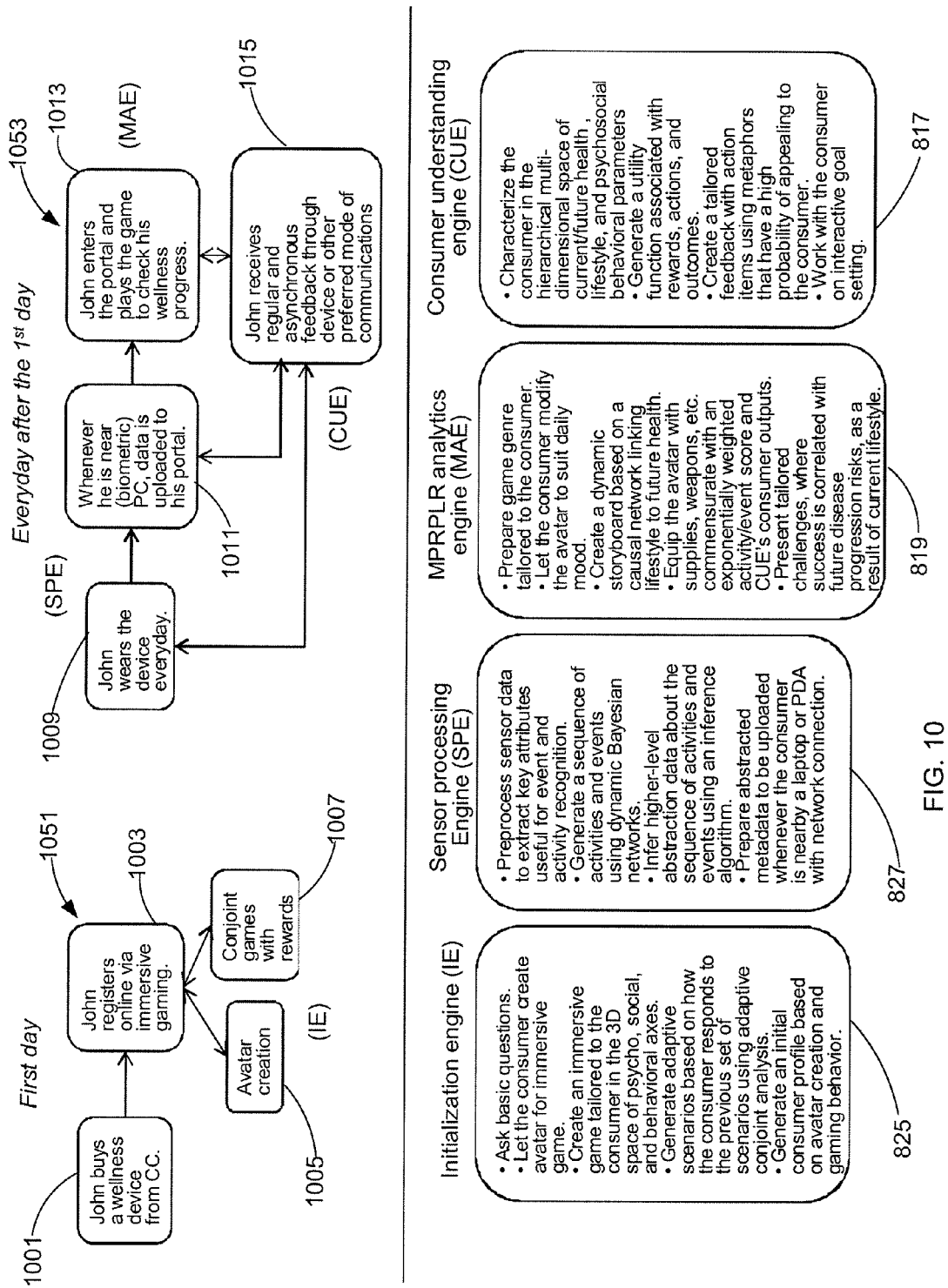
FIG. 10 shows an integrated consumer experience flowchart to accelerate the pace of learning causal relations between lifestyle and wellness as well as how the four engines work to enhance the consumer experience.

The following discussion illustrates an exemplary scenario for a participant (consumer) to show the relationships among the above-mentioned concepts. FIG. 10 shows integrated experience flowcharts 1051 and 1053 for a participant to accelerate the pace of learning causal relations between lifestyle and wellness as well as illustrate the interrelationship of engines 817, 819, 825, and 827 for enhancing the participant's experience. The exemplary scenario focuses on causal network 900, in which the participant is pre-diabetic with BMI of 29 kg/m² with a poor behavior/lifestyle (BL) score. However, the participant does not like the way he looks and wants to change his life.

With embodiments of the invention, engines 817, 819, 825, and 827 have the following functionalities:

Initialization Engine (IE) 825:
  Ask questions
  Let the participant (user) create an avatar for immersive game
  Create an immersive game tailored to the user in the 3D space of psycho, social, and behavior axes
  Generate adaptive scenarios based on how the user responds to the previous set of scenarios using adaptive conjoint analysis
  Generate an initial user profile based on avatar creation and gaming behavior Sensor Processing Engine (SPE) 827:
  Preprocess sensor data to extract key attributes useful for event and activity recognition
  Generate a sequence of activities and events using dynamic Bayesian networks
  Infer high-level abstraction data about the sequence of activities and events using an inference algorithm
  Prepare abstracted metadata to be uploaded whenever the user is nearby a laptop or PDA with network connection MPRPLR Analytics Engine (MAE) 819:
  Prepare game genre tailored to the user (participant)
  Let the user modify the avatar to suit daily need
  Create a dynamic storyboard based on a causal network linking lifestyle to future health
  Equip the avatar with supplies, weapons, etc commensurate with an exponentially weighted activity/event score and CUE's consumer outputs
  Present tailored challenges, where success is correlated with the future disease progression risks, as a result of current lifestyle Consumer Understanding Engine (CUE) 817:
  Characterize the user in the hierarchical multi-dimensional space of current/future health, lifestyle, and psychosocial behaviors parameters
  Generate a utility function associated with rewards, actions, and outcomes
  Create a tailored feedback with action items using metaphors that have a high probability of appealing to the user
  Work with the user on interactive goal setting On a sunny Saturday morning, he goes to Circuit City and buys a three-in-one health watch that senses speech, measures the level of activity using a 2-axis accelerometer, and synchronizes data with a SmartWellness Web (SWW) portal using WiMax (corresponding to step 1001 as shown in FIG. 10). At home, he logs into www.smartwellness.com (which a hypothetical website and corresponding to step 1003), expecting to answer a series of personal questions. Instead he is pleasantly surprised to be ushered into a virtual gaming environment (immersive user data collection environment).

The Virtual Game Fairy (VGF) asks John five questions: name, address, date of birth, e-mail address, and password since his laptop doesn't have a biometric login. Next John is immersed in a small adventure (corresponding to step 1007), where he needs to make choices to grab his trophy. While John is busy playing the game to win the trophy before it disappears, the VGF processes John's choices over time, game pacing, and other game behaviors to form an impression of him. Based on the following behaviors, the VGF forms certain impressions on John as shown in Table 1.

TABLE 1

IMPRESSIONS BASED ON BEHAVIOR

| Behavior | Impression |
| --- | --- |
| Recognizes instantly and likes to hang out with Steve Nash. | Likes basketball and we can use a basketball metaphor to talk to John. |
| Whenever there was an opportunity to form a small team to finish a task sooner in a credit- | Practical, shuns people in general, likes individual activities (he must |

TABLE 1-continued

IMPRESSIONS BASED ON BEHAVIOR

| Behavior | Impression |
| --- | --- |
| sharing mode, John declines and finishes the task himself. At the end, he prefers to accumulate virtual cash rewards instead of splurging in unique travel experience to an exotic locale with a Sports Illustrated swimsuit model. | enjoy watching basketball, not playing), some insights on the type of rewards to which he would react favorably |
| Out of three rare movie clips with synopses-Chungking Express, The Host, and Old Joy-he chose to watch The Host and rated it very high. | Enjoys watching the action-adventure genre with a monster possibly as an escape from reality, doesn't like movies that mimic or remind him of the real world |

As part of the immersive gaming experience, John creates an avatar (corresponding to step 1005) with certain characteristics that provide a number of additional insights about him. The behavioral similarities and differences between John and his alter ego will be evaluated over time to improve the confidence associated with making a number of crucial inferences about John.

After registration, John wears the device every day (step 1009). He feels energetic the following day and starts a day running 2 miles on a LifeFitness treadmill in 20 minutes. During lunch, he goes out to a South Indian restaurant with his co-workers, chatting about a technical subject that everyone feels passionate about. He attends several meetings and then goes home at about 6 PM. At home, he watches the ABC news while making a spaghetti dish. He notices that whenever he is near a secured network environment at home with a (biometric) laptop, the abstracted metadata summarizing his daily activities and social encounters are uploaded to the personal care portal automatically (step 1011). His curiosity piques, but he takes care of dinner first since he's hungry.

After dinner, John is curious about how his daily living can affect his future health. He logs into the SWW portal and is greeted by a voice to play an interactive game to check his daily progress (step 1013). He has an option of selecting a new avatar or going with the previous one. He selects a new avatar based on the character of King Leonidas in the movie 300. He then selects a game of enemy conquest against odds out of a menu of games with different genres.

Since John's behavior-lifestyle score is high today, he's rewarded with extra arrows and an upgraded armor for protection. On other days, depending on his social activities, he is given extra loyal soldiers to help him conquer the enemies. The MAE maintains and updates a list of available games, consumer profiles including daily behavioral/lifestyle context awareness (sent from the CUE layer), game-playing behaviors, and predictive analytics that perform the matching of rewards to games being played as a function of consumer profiles and trends in behavior and lifestyle. In addition the predictive analytics component undertakes the analysis of discrepancies between predicted behaviors upon rewards and actual ones to improve the matching process going forward.

After a couple of weeks, John gets bored and stops working out regularly. He has been ignoring occasional messages flashing on his wellness device. One day, he logs into the SWW portal and is funneled to a tunnel that lands him inside a medieval dungeon. He's surprised to see his avatar appear so haggard and old (step 1015). The Virtual Game Fairy (VGF) explains that what John sees now is the extrapolated trajectory of his wellness in ten years if he decides to stick to the current lifestyle given his current health status. The VGF encourages him to explore the new dreary environment for entertainment. Consumer feedback may be asynchronous (adheres to predefined or user-customizable feedback criteria), regular (once a day, for example), or on demand through the preferred or available communication channel.

Feeling spooked, John plays a game of escape with other prisoners in the dungeon. The first thing he notices is that his avatar is frail physically, requiring frequent rest while walking around to explore the environment and find an escape route. When he asks why using an IM to the VGF, the VGF explains that given his BMI and the extension of his current sedentary lifestyle, he is expected to develop metabolic syndrome, which can lead to diabetes and cardiovascular disease with significant functional declines from where he is today. Since the avatar is an extension of John down the road should he follow the current path, it is no wonder that the avatar is far from being in perfect health good enough to escape from the dungeon with the other prisoners.

Now that John understands the genesis of functional decline in his avatar, he changes the timeframe slider bar to understand the progression of functional decline. He notices that there is no precipitous drop that can be noticed immediately and acted upon; instead, he sees a gradual decline such that it is next to impossible to detect functional decline on a daily basis.

After several frustrating excursions, John is back in the dungeon with his avatar looking even more exhausted. The fidelity of facial expression in high resolution is amazing. He asks the VGF for an advice. She instructs John to be patient and work on making his daily routines more meaningful and impactful on his wellness—both mind and body. Taking this advice to heart, he works with the VGF to set up specific goals on fitness, social life, creativity, and spirituality.

As John works his way back to good health, he sees the immediate impact on the way his avatar looks, plays the game, and achieves results. Soon afterwards he notices changes in him.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

I claim:
1. A computer-implemented method comprising:
obtaining sensor data from a device that measures a level of physical activity undertaken by a user of the device;
classifying, by a computer, recent exercise behavior of the user as a particular type of exercise behavior based on sensor data collected between a time when the device began measuring the level of physical activity under- taken by the user and a time when the user began playing an immersive lifestyle-reward health game;

adjusting an ability of an avatar controlled by the user to compete within the immersive lifestyle-reward health game based on tradeoff decisions made by the user between two or more competing motivations within the immersive lifestyle reward health game and based on classifying the recent exercise behavior of the user as the particular type of exercise behavior based on the sensor data collected between the time when the device began measuring the level of physical activity undertaken by the user and the time when the user began playing the immersive lifestyle reward health game;

establishing a likely motivational hierarchy for the user controlling the avatar based at least on the trade-off decisions made within the immersive lifestyle-reward health game, wherein the likely motivational hierarchy specifies a likely relative importance, to the user, of the two or more competing motivations; and using the likely motivational hierarchy that is established for the user based at least on the trade-off decision made for the avatar within the immersive lifestyle-reward game to tailor a real-world health incentive program for the user.

2. The method of claim 1, further comprising:
determining that the user's recent exercise behavior represents less than a predetermined amount of exercise;
wherein altering the ability of the avatar comprises reducing the ability of the avatar relative to a default value for the ability, thereby increasing a level of difficulty for the lifestyle-reward health game.

3. The method of claim 1, further comprising:
determining that the user's recent exercise behavior represents at least a predetermined amount of exercise;
wherein altering the ability of the avatar comprises increasing the ability of the avatar relative to a default value for the ability, thereby decreasing a level of difficulty for the lifestyle-reward health game.

4. The method of claim 1, further comprising:
generating a profile for the user based on game decisions made by the user while playing the lifestyle-reward health game;
selecting a reward from a plurality of available rewards based on the user profile; and
presenting the reward to the user in conjunction with the user playing the lifestyle-reward health game.

5. The method of claim 1, wherein the device includes an accelerometer, and wherein the insight is based on the movement of the user detected by the accelerometer.

6. The method of claim 1, wherein the insight regarding the user's recent exercise behavior characterizes the user's exercise behavior since the user last played the lifestyle-reward health game.

7. The method of claim 1, wherein using the likely motivational hierarchy that is established for the user based at least on the trade-off decision made for the avatar within the immersive lifestyle-reward game to tailor a real-world health incentive program for the user comprises:
estimating a utility function based on the likely motivational hierarchy that is established for the user, wherein the utility function indicates an estimated impact on real-world behavioral change of the user in response to a motivation from the two or more competing motivations.

8. The method of claim 7, wherein estimating a utility function based on the likely motivational hierarchy that is established for the user further comprises:

determining an in-game performance difference exhibited by the avatar controlled by the user before and after receiving rewards as a result of the trade-off decisions made for the avatar within the immersive lifestyle-reward game.

9. The method of claim 1, wherein the two or more competing motivations comprise at least one of a financial-focused motivation and a health-focused motivation.

10. A system comprising:
one or more computers and one or more storage devices storing instructions that are operable, when executed by the one or more computers, to cause the one or more computers to perform operations comprising:
obtaining sensor data from a device that measures a level of physical activity undertaken by a user of the device,
classifying recent exercise behavior of the user as a particular type of exercise behavior based on sensor data collected between a time when the device began measuring the level of physical activity undertaken by the user and a time when the user began playing an immersive lifestyle-reward health game;
adjusting an ability of an avatar controlled by the user to compete within the immersive lifestyle-reward health game based on classifying the recent exercise behavior of the user as the particular type of exercise behavior based on the sensor data collected between the time when the device began measuring the level of physical activity undertaken by the user and the time when the user began playing the immersive lifestyle reward health game;
generating a scenario within the immersive lifestyle-reward game in which the user must make a trade-off decision for the avatar;
establishing a likely motivational hierarchy for the user controlling the avatar based at least on the trade-off decision made within the immersive lifestyle-reward health game, wherein the likely motivational hierarchy specifies a likely relative importance, to the user, of two or more competing motivations; and
using the likely motivational hierarchy that is established for the user based at least on the trade-off decision made for the avatar within the immersive lifestyle-reward game to tailor a real-world health incentive program for the user.

11. The system of claim 10,
wherein the operations further comprise determining that the user's recent exercise behavior represents less than a predetermined amount of exercise; and
wherein altering the ability of the avatar comprises reducing the ability of the avatar relative to a default value for the ability, thereby increasing a level of difficulty for the lifestyle-reward health game.

12. The system of claim 10,
wherein the operations further comprise determining that the user's recent exercise behavior represents at least a predetermined amount of exercise; and
wherein altering the ability of the avatar comprises increasing the ability of the avatar relative to a default value for the ability, thereby decreasing a level of difficulty for the lifestyle-reward health game.

13. The system of claim 10, wherein the operations further comprise:
generating a profile for the user based on game decisions made by the user while playing the lifestyle-reward health game;
selecting a reward from a plurality of available rewards based on the user profile; and presenting the reward to the user in conjunction with the user playing the lifestyle-reward health game.

14. The system of claim 10, wherein the device includes an accelerometer, and wherein the insight is based on the movement of the user detected by the accelerometer.

15. A non-transitory computer-readable medium storing software comprising instructions executable by one or more computers which, upon such execution, cause the one or more computers to perform operations comprising:
obtaining sensor data from a device that measures a level of physical activity undertaken by a user of the device,
classifying recent exercise behavior of the user as a particular type of exercise behavior based on sensor data collected between a time when the device began measuring the level of physical activity undertaken by the user and a time when the user began playing an immersive lifestyle-reward health game;
adjusting an ability of an avatar controlled by the user to compete within the immersive lifestyle-reward health game based on classifying the recent exercise behavior of the user as the particular type of exercise behavior based on the sensor data collected between the time when the device began measuring the level of physical activity undertaken by the user and the time when the user began playing the immersive lifestyle reward health game;
generating a scenario within the immersive lifestyle-reward game in which the user must make a trade-off decision for the avatar;
establishing a likely motivational hierarchy for the user controlling the avatar based at least on the trade-off decision made within the immersive lifestyle-reward health game, wherein the likely motivational hierarchy specifies a likely relative importance, to the user, of two or more competing motivations; and
using the likely motivational hierarchy that is established for the user based at least on the trade-off decision made for the avatar within the immersive lifestyle-reward game to tailor a real-world health incentive program for the user.

16. The medium of claim 15,
wherein the operations further comprise determining that the user's recent exercise behavior represents less than a predetermined amount of exercise; and
wherein altering the ability of the avatar comprises reducing the ability of the avatar relative to a default value for the ability, thereby increasing a level of difficulty for the lifestyle-reward health game.

17. The medium of claim 15,
wherein the operations further comprise determining that the user's recent exercise behavior represents at least a predetermined amount of exercise; and
wherein altering the ability of the avatar comprises increasing the ability of the avatar relative to a default value for the ability, thereby decreasing a level of difficulty for the lifestyle-reward health game.

18. The medium of claim 15, wherein the operations further comprise:
generating a profile for the user based on game decisions made by the user while playing the lifestyle-reward health game;
selecting a reward from a plurality of available rewards based on the user profile; and
presenting the reward to the user in conjunction with the user playing the lifestyle-reward health game.

19. The medium of claim 15, wherein the device includes an accelerometer, and wherein the insight is based on the movement of the user detected by the accelerometer.

20. A computer-implemented method, comprising:
receiving sensor data from a device that monitors real-life habits of a user of the device that impact the user's health;
evaluating, by one or more computers, the received sensor data to determine that recent habits of the user, between a time when the device began monitoring the real-life habits of the user and a time when the user began playing an immersive lifestyle-reward game, would place the user at risk for a chronic medical condition;
identifying one or more symptoms of the chronic medical condition;
modifying an ability of an avatar that is controlled by the user within the game to exhibit the one or more symptoms of the chronic medical condition;
generating a scenario within the immersive lifestyle-reward game in which the user must make a trade-off decision for the avatar;
establishing a likely motivational hierarchy for the user controlling the avatar based at least on the trade-off decision made within the immersive lifestyle-reward health game, wherein the likely motivational hierarchy specifies a likely relative importance, to the user, of two or more competing motivations; and
using the likely motivational hierarchy that is established for the user based at least on the trade-off decision made for the avatar within the immersive lifestyle-reward game to tailor a real-world health incentive program for the user.

21. The method of claim 20, further comprising:
modifying an appearance of the avatar to exhibit one or more symptoms of the chronic medical condition.

22. The method of claim 20, further comprising:
selecting a treatment based on the chronic medical condition; and
conveying information about the treatment to the user through the game.

23. The method of claim 22,
wherein the treatment comprises a change in the real-life habits of the user; and
wherein the method further comprises modifying the game to incentivize the user to make the change to the user's real-life habits.

* * * * *

UNITED STATES PATENT AND TRADEMARK OFFICE
CERTIFICATE OF CORRECTION

| | | |
|---|---|---|
| PATENT NO. | : 8,714,983 B2 | Page 1 of 1 |
| APPLICATION NO. | : 11/751856 | |
| DATED | : May 6, 2014 | |
| INVENTOR(S) | : David H. Kil | |

It is certified that error appears in the above-identified patent and that said Letters Patent is hereby corrected as shown below:

In the Claims

In claim 10, column 30, line 15, delete "device," and insert -- device; --, therefor.

In claim 15, column 31, line 11, delete "device," and insert -- device; --, therefor.

Signed and Sealed this
Twelfth Day of August, 2014

Michelle K. Lee
*Deputy Director of the United States Patent and Trademark Office*